US009549549B2

(12) United States Patent
Whitten et al.

(10) Patent No.: US 9,549,549 B2
(45) Date of Patent: Jan. 24, 2017

(54) ANTIMICROBIAL MATERIALS AND METHODS

(75) Inventors: David G. Whitten, Albuquerque, NM (US); Kirk S. Schanze, Gainesville, FL (US); Eunkyung Ji, Ervy le Chatel (FR); Dimitri Dascier, Ervy le Chatel (FR); Anand Parthasarathy, Gainsville, FL (US); Thomas S. Corbitt, Albuquerque, NM (US); Kirsten Cicotte, Albuquerque, NM (US); Elizabeth LeBleu Dirk, Albuquerque, NM (US); Xuzhi Zhu, Gainsville, FL (US)

(73) Assignees: STC.UNM, Albuquerque, NM (US); University of Florida Research Foundation, Inc., Gainesville, FL (US)

( * ) Notice: Subject to any disclaimer, the term of this patent is extended or adjusted under 35 U.S.C. 154(b) by 174 days.

(21) Appl. No.: 14/233,130

(22) PCT Filed: Aug. 3, 2012

(86) PCT No.: PCT/US2012/049613
§ 371 (c)(1),
(2), (4) Date: May 8, 2014

(87) PCT Pub. No.: WO2013/020096
PCT Pub. Date: Feb. 7, 2013

(65) Prior Publication Data
US 2014/0242148 A1    Aug. 28, 2014

Related U.S. Application Data

(60) Provisional application No. 61/514,791, filed on Aug. 3, 2011, provisional application No. 61/528,603, filed on Aug. 29, 2011, provisional application No. 61/559,232, filed on Nov. 14, 2011, provisional application No. 61/606,048, filed on Mar. 2, 2012, provisional application No. 61/661,261, filed on Jun. 18, 2012.

(51) Int. Cl.
| | | |
|---|---|---|
| *A01N 25/34* | (2006.01) | |
| *A61L 15/46* | (2006.01) | |
| *A01N 33/12* | (2006.01) | |
| *A01N 43/10* | (2006.01) | |
| *A01N 43/90* | (2006.01) | |
| *A01N 37/10* | (2006.01) | |

(52) U.S. Cl.
CPC .............. *A01N 25/34* (2013.01); *A01N 33/12* (2013.01); *A01N 37/10* (2013.01); *A01N 43/10* (2013.01); *A01N 43/90* (2013.01); *A61L 15/46* (2013.01); *A61L 2300/404* (2013.01)

(58) Field of Classification Search
CPC ........ A01N 25/34; A01N 33/12; A01N 37/10; A01N 43/10; A01N 43/90
See application file for complete search history.

(56) References Cited

U.S. PATENT DOCUMENTS

| | | |
|---|---|---|
| 4,251,386 A | 2/1981 | Saeki et al. |
| 5,449,809 A | 9/1995 | Wingert et al. |
| 5,489,400 A | 2/1996 | Liu et al. |
| 6,743,640 B2 | 6/2004 | Whitten et al. |
| 7,122,383 B2 | 10/2006 | Jones et al. |
| 8,455,265 B2 | 6/2013 | Whitten et al. |
| 8,598,053 B2 | 12/2013 | Whitten et al. |
| 8,618,009 B2 | 12/2013 | Schanze et al. |
| 8,753,570 B2 | 6/2014 | Whitten et al. |
| 9,005,540 B2 | 4/2015 | Schanze et al. |
| 2003/0134959 A1 | 7/2003 | Hancock et al. |
| 2003/0168756 A1 | 9/2003 | Balkus, Jr. et al. |
| 2003/0178607 A1 | 9/2003 | Swager et al. |
| 2004/0241768 A1 | 12/2004 | Whitten et al. |
| 2005/0059168 A1 | 3/2005 | Bazan et al. |
| 2005/0148254 A1* | 7/2005 | Lu .......................... A01N 33/12 442/123 |
| 2006/0120923 A1 | 6/2006 | Swager et al. |

(Continued)

FOREIGN PATENT DOCUMENTS

| | | | |
|---|---|---|---|
| WO | WO-2008143731 A2 | 11/2008 | |
| WO | WO-2009/158606 A2 | 12/2009 | |
| WO | WO 2009158606 A2 * | 12/2009 | ............. A01N 33/12 |
| WO | WO-2009158606 A9 | 12/2009 | |
| WO | WO-2010/054304 A2 | 5/2010 | |
| WO | WO-2011/044580 A3 | 4/2011 | |
| WO | WO-2012/009472 A2 | 1/2012 | |
| WO | WO-2013020096 A2 | 2/2013 | |
| WO | WO-2013020096 A3 | 2/2013 | |

OTHER PUBLICATIONS

Corbitt, T.S. et al. "Conjugated Polyelectrolyte Capsules: Light-Activated Antimicrobial Micro Roach Motels" ACS Applied Materials & Interfaces 2009, 1 (1) 48-52 (published online Nov. 24, 2008).*

(Continued)

*Primary Examiner* — Timothy Thomas
*Assistant Examiner* — Andrew S Rosenthal
(74) *Attorney, Agent, or Firm* — Schwegman Lundberg & Woessner, P.A.

(57) ABSTRACT

The invention provides methods and materials for decontamination of surfaces and fabrics, such as non-woven fabrics, that are contaminated with infestations of microorganisms such as bacteria. Biocidal oligomers having conjugated oligo-(aryl/heteroaryl ethynyl) structures and comprising at least one cationic group can be used to decontaminate infested surfaces in the presence of oxygen and, optionally, illumination. Fibers incorporating biocidal oligomers having conjugated oligo-(aryl/heteroaryl ethynyl) structures and comprising at least one cationic group, wherein the oligomer is physically associated with or covalently bonded to, or both, the fiber-forming polymer can be used to form non-woven mats. Biocidal non-woven mats prepared by methods of the invention, incorporating the biocidal oligomers, can be used to suppress bacterial growth in wound and surgical dressings and personal hygiene products.

15 Claims, 16 Drawing Sheets

(56) References Cited

U.S. PATENT DOCUMENTS

| | | | |
|---|---|---|---|
| 2006/0175193 A1 | 8/2006 | Inganas et al. | |
| 2007/0215841 A1 | 9/2007 | Ford et al. | |
| 2008/0090021 A1 | 4/2008 | Long et al. | |
| 2010/0285081 A1* | 11/2010 | Chen | D01D 5/0038 424/405 |
| 2011/0159605 A1 | 6/2011 | Whitten et al. | |
| 2011/0223058 A1 | 9/2011 | Whitten et al. | |
| 2011/0293470 A1 | 12/2011 | Schanze et al. | |
| 2012/0271023 A1 | 10/2012 | Whitten et al. | |
| 2013/0273800 A1 | 10/2013 | Whitten et al. | |
| 2014/0086795 A1 | 3/2014 | Schanze et al. | |

OTHER PUBLICATIONS

Zhou, Z. et al. ""End-Only" Functionalized Oligo(phenylene ethynylene)s: Synthesis, Photophysical and Biocidal Activity" J. P. Chem. Lett. 2010, 1, 3207-3212.*
U.S. Appl. No. 12/529,390, Examiner Interview Summary mailed Jan. 31, 2012, 3 pgs.
U.S. Appl. No. 12/529,390, Examiner Interview Summary mailed Nov. 13, 2012, 3 pgs.
U.S. Appl. No. 12/529,390, Non Final Office Action mailed Jul. 18, 2012, 7 pgs.
U.S. Appl. No. 12/529,390, Non-Final Office Action mailed Nov. 1, 2011, 11 pgs.
U.S. Appl. No. 12/529,390, Notice of Allowance mailed Feb. 5, 2013, 10 pgs.
U.S. Appl. No. 12/529,390, Preliminary Amendment mailed Sep. 1, 2009, 13 pgs.
U.S. Appl. No. 12/529,390, Response filed May 1, 2012 to Non Final Office Action mailed Nov. 1, 2011, 19 pgs.
U.S. Appl. No. 12/529,390, Response filed Dec. 18, 2012 to Non Final Office Action mailed Jul. 18, 2012, 16 pgs.
U.S. Appl. No. 13/001,478 , Response filed Dec. 19, 2013 to Non Final Office Action mailed Oct. 3, 2013, 10 pgs.
U.S. Appl. No. 13/001,478, Non Final Office Action mailed Oct. 3, 2013, 6 pgs.
U.S. Appl. No. 13/001,478, Notice of Allowance mailed Jan. 31, 2014, 7 pgs.
U.S. Appl. No. 13/001,478, Response filed Jul. 11, 2013 to Restriction Requirement mailed Jun. 13, 2013, 9 pgs.
U.S. Appl. No. 13/001,478, Restriction Requirement mailed Jun. 13, 2013, 7 pgs.
U.S. Appl. No. 13/128,571 ,Response filed May 13, 2013 to Non Final Office Action mailed Feb. 13, 2013, 12 pgs.
U.S. Appl. No. 13/128,571, Response filed Nov. 19, 2012 to Restriction Requirement mailed Oct. 17, 2012, 6 pgs.
U.S. Appl. No. 13/128,571, Non Final Office Action mailed Feb. 13, 2013, 10 pgs.
U.S. Appl. No. 13/128,571, Notice of Allowance mailed Aug. 28, 2013, 9 pgs.
Serial No, 13/128,571, Preliminary Amendment filed May 10, 2011, 5 pgs.
U.S. Appl. No. 13/128,571, Restriction Requirement mailed Oct. 17, 2012, 6 pgs.
U.S. Appl. No. 13/503,067, Response filed Mar. 11, 2013 to Non Final Office Action mailed Oct. 10, 2012, 11 pgs.
U.S. Appl. No. 13/503,067, Response filed Jul. 11, 2013 to Final Office Action mailed Jun. 6, 2013, 7 pgs.
U.S. Appl. No. 13/503,067, Final Office Action mailed Jun. 6, 2013, 11 pgs.
U.S. Appl. No. 13/503,067, Non Final Office Action mailed Oct. 10, 2012, 11 pgs.
U.S. Appl. No. 13/503,067, Notice of Allowance mailed Aug. 2, 2013, 10 pgs.
U.S. Appl. No. 13/809,573, Response filed Sep. 24, 2015 to Restriction Requirement mailed Jul. 24, 2015, 9 pgs.
U.S. Appl. No. 13/809,573, Restriction Requirement mailed Jul. 24, 2015, 7 pgs.
U.S. Appl. No. 14/092,409, Notice of Allowance mailed Dec. 10, 2014, 10 pgs.
European Application Serial No. 09771137.8, Office Action mailed Feb. 9, 2011, 1 pg.
European Application Serial No. 09771137.8, Office Action mailed Feb. 14, 2011, 2 pgs.
European Application Serial No. 09771137.8, Office Action mailed Mar. 3, 2011, 1 pg.
European Application Serial No. 09771137.8, Office Action mailed Mar. 16, 2011, 1 pg.
European Application Serial No. 09771137.8, Response filed Feb. 18, 2011 to Office Action mailed Feb. 9, 2011, 6 pgs.
International Application Serial No. PCT/US2008/002756, International Preliminary Report on Patentability mailed Sep. 1, 2009, 6 pgs.
International Application Serial No. PCT/US2008/002756, International Search Report mailed Feb. 25, 2009, 2 pgs.
International Application Serial No. PCT/US2008/002756, Written Opinion mailed Feb. 25, 2009, 5 pgs.
International Application Serial No. PCT/US2009/048838, International Preliminary Report on Patentability mailed Jan. 5, 2011, 7 pgs.
International Application Serial No. PCT/US2009/048838, International Search Report mailed Apr. 30, 2010, 4 pgs.
International Application Serial No. PCT/US2009/048838, Written Opinion mailed Apr. 30, 2010, 6 pgs.
International Application Serial No. PCT/US2009/063715, International Preliminary Report on Patentability mailed May 10, 2011, 6 pgs.
International Application Serial No. PCT/US2009/063715, International Search Report mailed May 27, 2010, 4 pgs.
International Application Serial No. PCT/US2009/063715, Written Opinion mailed May 27, 2010, 5 pgs.
International Application Serial No. PCT/US2010/052332, International Preliminary Report on Patentability mailed Apr. 11, 2012, 7 pgs.
International Application Serial No. PCT/US2010/052332, International Search Report mailed Jun. 24, 2011, 4 pgs.
International Application Serial No. PCT/US2010/052332, Written Opinion mailed Jun. 24, 2011, 6 pgs.
International Application Serial No. PCT/US2011/043908, International Preliminary Report on Patentability mailed Jan. 15, 2013, 7 pgs.
International Application Serial No. PCT/US2011/043908, International Search Report and Written Opinion mailed Apr. 6, 2012, 11 pgs.
Arnt, Lachelle, et al., "New Poly(phenyleneethynylene)s with Cationic, Facially Amphiphilic Structures", Journal of the American Chemical Society,124(26), (2002), 7664-7665.
Bruns, R., et al., "Chapter 3—R&D in material protection: New biocides", In: Directory of Microbicides for the Protection of Materials—A Handbook, Paulus, W., Editor, (2005), 25-46.
Choi, W. S., et al., "Synthesis of Two Types of Nanoparticles in Polyelectrolyte Capsule Nanoreactors and Their Dual Functionality", J. Am. Chem. Soc., 127, (2005), 16136-16142.
Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.
Corbitt, Thomas S., et al., "Conjugated Polyelectrolyte Capsules: Light-Activated Antimicrobial Micro "Roach Motels"†", ACS Appl. Mater. Interfaces, 1(1), (2009), 48-52.
De Geest, B. G., et al., "Release mechanisms for polyelectrolyte capsules", Chem. Soc. Rev., 36, (2007), 636-649.
Fan, Qu-Li, et al., "Water-Soluble Cationic Poly(p-phenyleneethynylene)s (PPEs): Effects of Acidity and ionic Strength on Optical Behavior.", Macromolecules.vol. 38, (2005), 2927-2936.
Galaev, Igor Y., "'Smart' polymers in biotechnology and medicine", Russian Chemical Reviews, 64(5), (1995), 471-489.
George, Wayne N., et al., "Amplified fluorescence quenching in high ionic strength media.", Soft Matter. vol. 3, (2007), 1381-1387.

(56) References Cited

OTHER PUBLICATIONS

Hoffman, Allan S., "Bioconjugates of Intelligent Polymers and Recognition Proteins for Use in Diagnostics and Affinity Separations", Clinical Chemistry, 46:9, (2000), 1478-1486.

Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.

Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C., 113(2), (2009), 755-764.

Lu, L. et al., "Biocidal Activity of a Light-Absorbing Fluorescent Conjugated Polyelectrolyte", Langmuir, 21, (2005), 10154-10159.

Schild, H. G., "Poly(N-Isopropylacrylamide): Experiment, Theory and Application", Prog. Polym. Sci., 17, (1992), 163-249.

Tan, C, et al., "Photophysics, aggregation and amplified quenching of a water-soluble poly (phenylene ethynylene)", Chem. Commun., (2002), 446-447.

Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.

Tang, Yanli, et al., "Synthesis. Self-Assembly, and Photophysical Behavior of Oligo Phenylene Ethynylenes: From Molecular to Supramolecular Properties", Langmuir, 25(1), (2009), 21-25.

Tew, G. N, et al., "", Biochimica et Biophysica Acta 2006, (2006), 1387-1392.

Tiller, J. C., et al., "Designing surfaces that kill bacteria on contact", Proc. Natl. Acad. Sci. USA, 98(11), (May 22, 2001), 5981-5985

Tong, W., et al., "Single Polyelectrolyte Microcapsules Fabricated by Glutaraldehyde-Mediated Covalent Layer-By-Layer Assembly", Macromol. Rapid Commun., 27, (2006), 2078-2083.

Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.

Wang, Z., et al., "Preparation and application of single polyelectrolyte microcapsules possessing tunable autofluorescent properties.", Colloids and Surfaces A: Physicochemical and Engineering Aspects, 329, (2008), 58-66.

Yang, Chaoyong James, et al., "Direct Synthesis of an Oligonucleotide-Poly-(phenylene ethynylene) Conjugate with a Precise One-to-One Molecular Ratio", Angew. Chem Int. Ed, 44, (2005), 2572-2576.

Zhu, Huiguang, et al., "Synthesis of Size-Controlled Monodisperse Manganese Carbonate Microparticles as Templates for Uniform Polyelectrolyte Microcapsule Formation.", Chem. Mater., 17, (2005), 2323-2328.

U.S. Appl. No. 13/809,573, filed Mar. 6, 2013, Structure, Synthesis, and Applications for Oligo Phenylene Ethynylenes (OPEs).

International Application Serial No. PCT/US2012/049613, International Search Report mailed Feb. 26, 2013, 3 pgs.

International Application Serial No. PCT/US2012/049613, Written Opinion mailed Feb. 26, 2013, 7 pgs.

International Application Serial No. PCT/US2012/049613, International Preliminary Report on Patentability mailed Feb. 13, 2014, 9 pgs.

Antoci, Jr., Valentin, et al., "Vancomycin covalently bonded to titanium alloy prevents bacterial colonization", Journal of Orthopaedic Research, 25(71, (2007), 858-866.

Beckloff, Nicholas, et al., "Activity of an Antimicrobial Peptide Mimetic against Planktonic and Biofilm Cultures of Oral Pathogens", Antimicrobial Agents and Chemotherapy, 51(11), (2007), 4125-4132

Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63(1), (2010), 116-124.

Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.

Chemburu, Sireesha, et al., "Light-Induced Biocidal Action of Conjugated Polyelectrolytes Supported on Colloids", Langmuir, 24(19), (2008), 11053-11062.

Corbitt, Thomas S., et al., "Light and dark biocidel activity of cationic poly(arylene ethynylene) conjugated polyelectrolytes", Photochem. Photobiol. Sci., 8(7), (2009), 998-1005.

Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.

Dascier, Dimitri, et al., "Efficacy of End-Only-Functionalized Oligo(arylene-ethynylene)s in Killing Bacterial Biofilms", Langmuir, 28(31), (2012), 11286-11290.

Donlan, Rodney M., et al., "Microbial Life on Surfaces", Emerging Infectious Diseases, 8(9), (2002), 881-890.

Eun, Ye-Jin, et al., "Fabrication of Microbial Biofilm Arrays by Geometric Control of Cell Adhesion", Langmuir, 25(8), (2009), 4643-4654.

Gao, Yuan, et al., "Recent Advances in Antimicrobial Treatment of Textiles", Textile Research Journal, 78(1), (2008), 60-72.

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hortholary, Cédric, et al., "An Approach to Long and Unsubstituted Molecular Wires: Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ji, Eunkyung, et al., "Antibacterial Activity of Conjugated Polyelectrolytes with Variable Chain Lengths", Langmuir, 27(17), (2011), 10763-10769.

Ji, Eunkyung, et al., "Light and Dark-Activated Biocidal Activity of Conjugated Polyelectrolytes", ACS Applied Materials & Interfaces, 3, (2011), 2820-2829.

Kenawy, El-Refaie, et al., "The Chemistry and Applications of Antimicrobial Polymers: A State-of-the-Art Review", Biomacromolecules, 8(2, (2007), 1359-1384.

Kolb, Hartmuth C., et al., "Click Chemistry: Diverse Chemical Function from a Few Good Reactions", Angew. Chem. Int. Ed., 40, (2001), 2004-2021.

Leach, Michelle K., et al., "Electrospinning Fundamentals: Optimizing Solution and Apparatus Parameters", Journal of Visualized Experiments, 47, (2011), 4 pgs.

Lindsay, D., et al., "Bacterial biofilms within the clinical setting: what healthcare professionals should know", Journal of Hospital Infection, 64, (2006), 313-325.

Lu, Timothy K., et al., "Dispersing biofilms with engineered enzymatic bacteriophage", Proc. Natl. Acad. Sci. USA, 104(27), (2007), 11197-11202.

McQuade, D. Tyler, et al., "Signal Amplification of a Turn-On Sensor: Harvesting the Light Captured by a Conjugated Polymer", J. Am. Chem. Soc., 122(49), (2000), 12389-12390.

Notestein, Justin M., et al., "Covalent Grafting of m-Phenylene-Ethynylene Oligomers to Oxide Surfaces", Chem. Mater., 22, (2010), 5319-5327.

Ogawa, Katsu, et al., "Conjugated Polyelectrolyte-Grafted Silica Microspheres", Langmuir, 23(8), (2007), 4541-4548.

Olson, Merle E., et al., "Biofilm bacteria: formation and comparative susceptibility to antibiotics", Canadian Journal of Veterinary Research-Revue Canadienne De Recherche Veterinaire, 66, (2002), 86-92.

Pasquier, Nicolas, et al., "From Multifunctionalized Poly(ethylene Imine)s toward Antimicrobial Coatings", Biomacromolecules, 8, (2007), 2874-2882.

(56) References Cited

OTHER PUBLICATIONS

Potera, Carol, "C. Microbiology—Forging a Link Between Biofilms and Disease", *Science*, 283(5409), (1999), 1837-1939.

Stewart, Philip S., et al., "Physiological heterogeneity in biofilms", *Nature Reviews Microbiology*, 6(3), (Mar. 2008), 199-210.

Tang, Yanli, et al., "Light-induced antibacterial activity of symmetrical and asymmetrical oligophenylene ethynylenes", *Langmuir*, 27(8), (2011), 4956-4962.

Valle, Jaione, et al., "Broad-spectrum biofilm inhibition by a secreted bacterial polysaccharide", *Proc. Natl. Acad. Sci. USA*, 103(33), (2006), 12558-12563.

Wang, Ying, et al., "Direct Visualization of Bactericidal Action of Cationic Conjugated Polyelectrolytes and Oligomers", *Langmuir*, 28(1), (2012), 65-70.

Zhang, Lian-Hui, et al., "Quorum sensing and signal interference: diverse implications", *Molecular Microbiology*, 53(6), (2004), 1563-1571.

Zhao, Xiaoyong, et al., "Variable Band Gap Poly(arylene ethynylene) Conjugated Polyelectrolytes", *Macromolecules*, 39(19), (2006), 6355-6366.

Zhou, Zhijun, et al., "End-Only Functionalized Oligo(phenylene ethynylene)s: Synthesis, Photophysical and Biocidal Activity", *Journal of Physical Chemistry Letters*, 1(21), (2010), 3207-3212.

U.S. Appl. No. 13/809,573, Non Final Office Action mailed Jan. 22, 2016, 13 pgs.

U.S. Appl. No. 13/809,573, Preliminary Amendment filed Jan. 10, 2013, 9 pgs.

Wang, Ying, et al., "Membrane Perturbation Activity of Cationic Phenylene Ethynylene Oligomers and Polymers", Langmuir Letter, 26(15), (2010), 12509-12514.

Zhinjou, Zhou, "Studies of a cyanine-based biosensor and light-induced antibacterial activities of oligophenyleneethynylenes", Dissertation, Chemistry, University of New Mexico, Albuquerque, NM, (Dec. 2010), 165 pgs.

\* cited by examiner

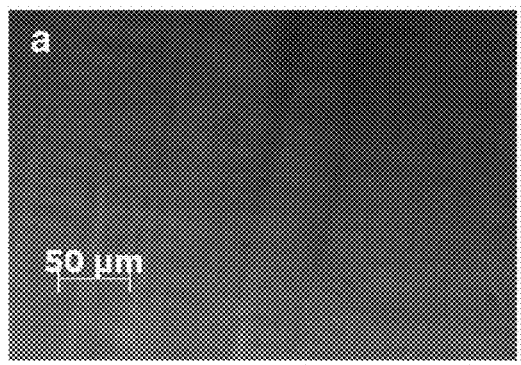 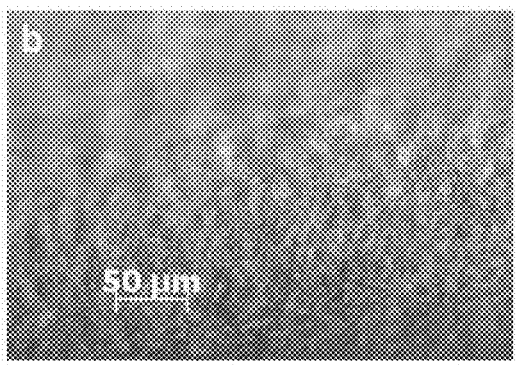
Fig. 4A  Fig. 4B
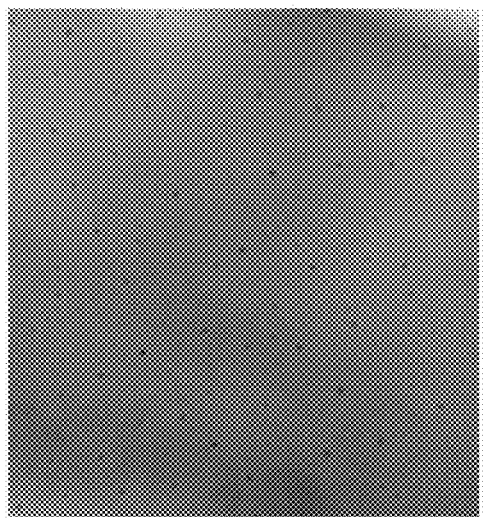 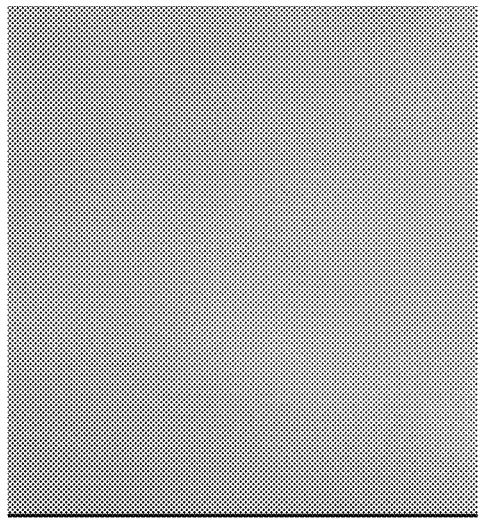
Fig. 5  Fig. 6

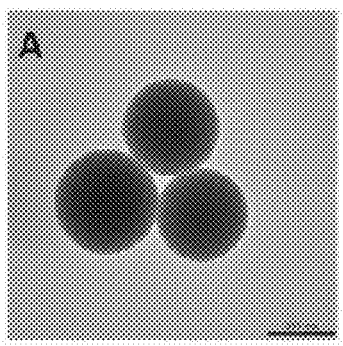
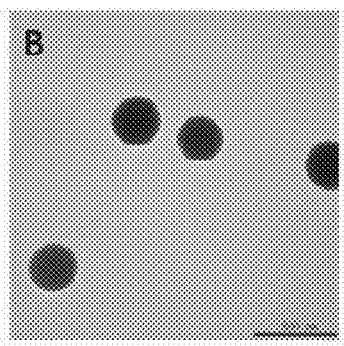
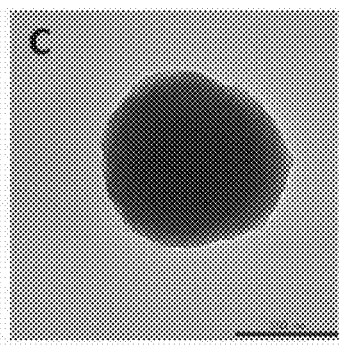
*Fig. 19A*  *Fig. 19B*  *Fig. 19C*
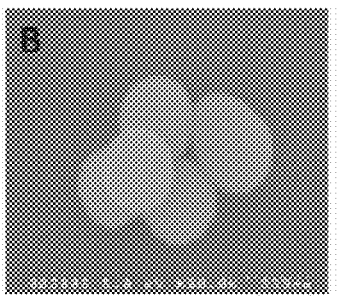
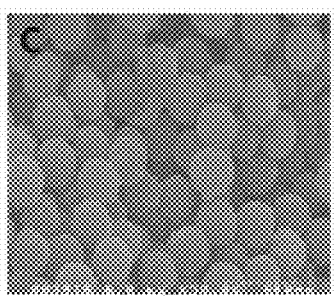
*Fig. 20A*  *Fig. 20B*  *Fig. 20C*

ANTIMICROBIAL MATERIALS AND METHODS

CROSS-REFERENCE TO RELATED APPLICATIONS

This application is a U.S. National Stage Application under 35 U.S.C. 371 from International Application No. PCT/US2012/049613, filed Aug. 3, 2012, which claims the benefit of priority of U.S. provisional applications, Ser. No. 61/514,791 filed Aug. 3, 2011; 61/528,603 filed Aug. 29, 2011; 61/559,232 filed Nov. 14, 2011; 61/606,048 filed Mar. 2, 2012; and 61/661,261 filed Jun. 18, 2012; the disclosures of which are incorporated herein by reference in their entireties.

STATEMENT OF GOVERNMENT SUPPORT

This invention was made with government support under W911NF07-1-0079, awarded by the Defense Threat Reduction Agency. The U.S. government has certain rights in the invention.

BACKGROUND

Antimicrobial treatment of materials is becoming an increasingly desirable mechanism for combating microbial pathogens. Microbial pathogens can be present on surfaces, e.g., bacterial biofilms disposed on the surface of materials such as metal, plastic, glass, wood, and the like, such as medical or food preparation tools or work areas; and microbial pathogens can be disposed within porous materials such as fibers, fabrics, and the like, such as wound treatment materials. Contamination of materials presents significant medical and public health risks, and biocidal treatment of surfaces and materials is vital, such as in blocking person to person transmission of diseases caused by microbial pathogens, in preventing infection of wounds by pathogens in the environment, in avoiding microbially-mediated food poisoning arising through contact of foodstuffs with contaminated work surfaces or personnel. Porous materials, such as fibers and fabrics, can be particularly difficult to block from microbial contamination, as the microorganisms can be protected from superficial sterilization procedures by the material itself. It is also important to develop materials having intrinsic antimicrobial properties that can avoid or reduce contamination over a period of time.

For example, surfaces of materials, such as food handling workspaces, surgical tools and equipment, and biological substrates such as the living tissues of patients, can be contaminated with bacterial biofilms. Bacterial biofilms are aggregates of bacteria in which cells adhere to each other on a surface and produce extracellular polymer matrix. The bacterial cells growing in biofilms are physiologically different from planktonic organism (freely suspended in a liquid medium); bacteria in biofilms can exhibit slow growth rates and higher resistance to antimicrobials, causing public health problems. Additionally biofilms naturally develop on living and inanimate surfaces. Biofilms can be found anywhere and widely involved in various infections in the body such as middle-ear infections, formation of dental plaque, and infections of indwelling medical devices.

Bacterial biofilms are aggregates of microbial cells adhered to one-another on a surface, producing an extracellular polymeric substance matrix.[1,2] The bacterial cells growing in biofilms are physiologically distinct from planktonic bacteria (freely suspended in a liquid medium) and a major source of public health problems.[2,3] Bacteria in these biofilms have slow growth rates and increased resistance to antimicrobials and the host defense systems. Additionally biofilms naturally develop on all types of surfaces: both living and inanimate surfaces. Biofilms can be associated with various microbial infections in the body such as dental plaque, kidney infections, urinary tract infections and infections of indwelling medical devices.[2,4]

Although several techniques[5-9] have been developed to prevent biofilm formation and to produce disinfection on surfaces, it is difficult to completely inhibit biofilm formation due to the physiological heterogeneity of bacteria in biofilms and their resistance to antibiotics.[10,11] Therefore, demand for new antimicrobials has been growing to prevent and eradicate biofilms.

Porous materials such as fibers and fabrics made therefrom can harbor and transmit microbial contaminants, so a treatment of such materials that can help prevent microbial contamination of the fabric and subsequent transmission, e.g., to tissue of a patient, such as healing wound tissue, would provide therapeutic benefits. Efforts have been made to develop fabrics having intrinsic biocidal activity.[15] These include not only those used in healthcare settings, but also those used to enhance personal hygiene and prevent deterioration of fabric. Among the most effective strategies are those using heavy metals and their salts, quaternary ammonium compounds, polyhexamethylene biguanides, triclosan, N-halamine compounds, and peroxyacids. While all are effective, all have substantial drawbacks, including the need for regeneration (N-halamines, peroxyacids), low biocidal activity (triclosan, PHMB), toxic byproducts (triclosan) and development of resistant strains.

SUMMARY

The present invention is directed in various embodiments to materials and methods that can be used to decontaminate surfaces that are contaminated with microbial infestation, such as in medical and food preparation uses, and to block contamination of and to decontaminate fabrics that are contaminated or are at risk for contamination with microorganisms, such a surgical and wound dressings, personal hygiene products, and the like.

The invention can provide, in various embodiments, the use of cationic end-only functionalized oligo(arylene-ethynylene)s (EO-OPEs) for preventing and eliminating *Escherichia coli* (*E. coli*) biofilms. *E. coli* infections (hospital and community acquired) are posing an increasing threat to health care systems.[12]

The present invention can provide, in various embodiments, methods of controlling populations of microorganisms within porous or absorbent materials, e.g. non-woven fabrics, wherein biocidal oligomers are applied to or disposed with the porous or absorbent materials. The biocidal oligomers exhibit potent and non-selective toxicity versus a wide range of microorganisms such as bacteria and fungi and quasi-organisms such as viruses, and the invention provides methods of decontaminating materials having populations of microorganisms and/or viruses, and methods of preventing growth of populations of microorganisms on or within the substrates.

In various embodiments, the invention provides methods whereby surfaces contaminated with biofilms incorporating harmful bacteria and the like can be sterilized; for example, by the use of "end-only" (EO) cation-functionalized oligomers, as described more fully below. These EO cationic oligo-(aryl/heteroaryl ethynylenes) have surprisingly been found to be especially effective for this purpose, compared to related substances. In other embodiments, the invention provides fibers and method for producing fibers comprising biocidal oligomers, either associated or covalently bonded thereto, which can be used for forming non-woven mats or fabrics, or can be used for forming woven fabrics, providing textile-like materials having antibacterial properties, that can be used in various applications when suppression or elimination of microbial infestation is desired.

Biocidal oligomers that can be used in carrying out methods of the invention can comprise oligomers containing two or more conjugated aryl/heteroaryl ethynyl units, substituted with one or more quaternary ammonium group. Compounds of this formula can be used to decontaminate a surface contaminated with a bacterial biofilm, or can be incorporated covalently or non-covalently into an absorbent material such as a non-woven fabric to kill microorganisms which may come in contact with the fabric. Biocidal oligomers useful for carrying out methods of the invention are of general formula (I)

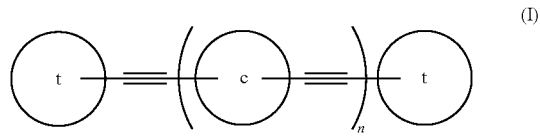

wherein each circle signifies an aryl or a heteroaryl ring system, wherein each circle respectively signifies an aryl or heteroaryl ring system, wherein each ring labeled t is a terminal ring system and each ring labeled c is a central ring system; n=1 to about 500, or n=1 to about 100, or n=1 to about 50, or n=1 to about 10, and the compound further comprises one or more moiety comprising a quaternary ammonium cationic group.

For killing of bacteria in biofilms, compounds of the above formula having a respective quaternary ammonium cationic group bonded to one or both terminal ring systems ("end-only" systems) have been unexpectedly found to be significantly superior in performance compared to related compounds lacking the end-only (EO) feature, with minimum inhibitory concentrations several fold less for killing biofilm bacteria than related compounds wherein the ammonium cationic groups are disposed elsewhere in the scaffold.

For conferring antimicrobial properties on fiber, such as in non-woven webs, compounds having the above scaffold and substituted with a cationic group, in various embodiments such as EO or non-EO, can be incorporated into fibers, either by physical assimilation or by covalent coupling reactions, to provide antimicrobial fibers and non-woven or woven fabrics formed therefrom.

Any ring of formula (I) can also bear further substituents; for example, a terminal aryl/heteroaryl ring can bear an unsubstituted ethynyl (acetylene) or alkylethynyl (higher alkynyl) group, which can be used in a "click chemistry" reaction with an azido group to covalently bond the oligomers to a functionalized solid or polymeric substrate.

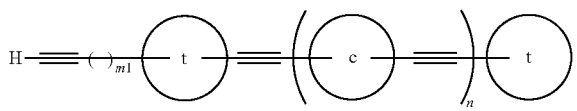

wherein m1 is 0 (ethynyl), or m1 is 1 to about 12 (higher alkynyl), providing a linker between the reactive ethynyl group for the acetylene/azide click reaction and the conjugated aryl/heteroaryl-ethynyl oligomers.

Any ring, terminal or central, can also bear substituents that have nucleophilic or electrophilic properties, such as hydroxyl, amino, thio, acyl, and the like, that are available for coupling with groups of complementary reactivity that are disposed on the fiber-forming polymer, for the formation of covalent bonds between the biocidal oligomer and the fiber-forming polymer. Rings can also bear substituents to modify solubility, light absorptivity, and the like, such as anionic groups (carboxylate, sulfonate), chromophoric groups (nitro, etc.), and the like.

Each aryl or heteroaryl group can be conjugated through the ethynyl (acetylenic) units with the adjacent aryl or heteroaryl groups. Preferably the system is sufficiently conjugated to have significant light absorptivity at wavelengths of visible and/or ultraviolet light. It is believed by the inventors that generation of singlet oxygen by light-activated excited states of the oligomers is a mode of antimicrobial activity. However, other mechanisms of antimicrobial toxicity may also be in action, as suggested by the antimicrobial bioactivity of some of the oligomers in the dark.

Singlet oxygen ($^1O_2$), the first electronically excited state of molecular oxygen (all pairs of bonding electrons having antiparallel spins), $O_2$, is well known to be a highly reactive gas under standard temperature and pressure (STP), e.g., in oxidation, addition to double bonds, and the like, and thus is a non-selective disruptor of complex organic assemblies, such as microorganisms. One mode of action can be attack of singlet oxygen on biological systems, such as an attack on cell membrane components, resulting in cell lysis and death. It is believed that development of resistance by bacterial populations to the effects of singlet oxygen is relatively unlikely, due to the diverse and devastating effects that the reactive material can have on the biochemical components of living systems.

A covalently bonded moiety comprising the quaternary ammonium group can be disposed at one or both termini of the linear oligomers, or on a central aryl or heteroaryl group. In various embodiments, cationic moiety can be bonded to the respective aryl or heteroaryl ring by a carbon-carbon bond, or through a phenolic oxygen atom as an ether. The cationic moiety can include a spacer unit, such as a (C1-C6)alkyl chain or a (C1-C6)alkoxy chain, connecting the ammonium nitrogen atom to the ring.

The biocidal oligomers can be non-covalently associated or covalently bound to various substrates, which in various embodiments are disclosed and claimed herein. The materials incorporating the oligomers can be porous/permeable materials such as non-woven fabrics incorporating fibers of various types that are associated or covalently bonded to the biocidal oligomers, e.g., as can be used in wound dressings, garments, personal hygiene products, and the like The fiber-forming substances can be synthetic polymers, such as polycaprolactone (PCL), poly-alpha-hydroxyesters, e.g., poly-lactic-glycolic acid (PLGA), poly-lactic acid (PLA), poly-glycolic acid (PGA), other aliphatic polyesters such as glycol-type polyesters of dibasic aliphatic diacids, aromatic polyesters such as glycol-type polyesters of dibasic aromatic acids (terephthalate, etc.) polyvinyl alcohol (PVA), polyethylene oxide (PEO), or polyolefins such as polyethylene, polypropylene, polyethylene/polypropylene copolymers, polystyrene (PS), and the like; or the fiber-forming substances can be natural materials such as cellulose, chitosan, alginate, gelatin, and the like.

Fibrous materials in which the biocidal oligomers are covalently bonded to the fiber substrate can be made using "click chemistry," as described herein, e.g., using oligomers with terminal ethynyl units to couple to azide-functionalized polymer, synthetic and natural. Such materials can be used when microbial contamination of the material is undesirable, such as for wound dressings, garments, personal hygiene products, and the like.

The invention further provides, in various embodiments, methods of making antimicrobial materials incorporating the biocidal oligomers, such as methods of manufacturing fibers incorporating the biocidal oligomers by various spinning techniques for use in preparation of antimicrobial non-woven fabrics. For example, for such uses, biocidal oligomers of formula (I) that incorporate the cationic ammonium group bonded to a central aryl/heteroaryl ring have been found to be particularly effective.

In various embodiments, the invention provides a method of killing biofilms comprising bacteria disposed on a surface, comprising contacting the biofilm with an effective amount of a biocidal oligomer. For example, a biocidal oligomers being the moiety comprising the cationic ammonium group can be bonded to one or both terminal aryl/heteroaryl groups for this use, as such "end-only" oligomers have been found to be particularly suitable for biocidal activity versus bacterial biofilms, as discussed below.

BRIEF DESCRIPTION OF THE FIGURES

FIG. 4 shows molecular models of EO-OPEs generated by using MM2 molecular mechanics in Chem3D Pro (version 10.0). Hydrogen atoms omitted for clarity. (4A) Oligomer (B), (4B) oligomer (C), (4C) oligomer (D) and (4D) oligomer (E) energy minimized structure of a single chain.

FIGS. 5A and 5B are bright-field microscopy images of E. coli biofilm growing on the peg surface of CBD. (A) Peg surface without biofilm. (B) Peg surface after 24 h incubation with E. coli.

For FIGS. 6-17, experiments were conducted to test the antimicrobial activity of the electrospun OPE/PCL mat. PCL only and OPE/PCL materials were exposed under both light and dark conditions to an E. coli culture and then stained with SYTOX Green, which stains only the dead bacteria. The stained bacteria were then observed with a FITC filter.

Figure 7:
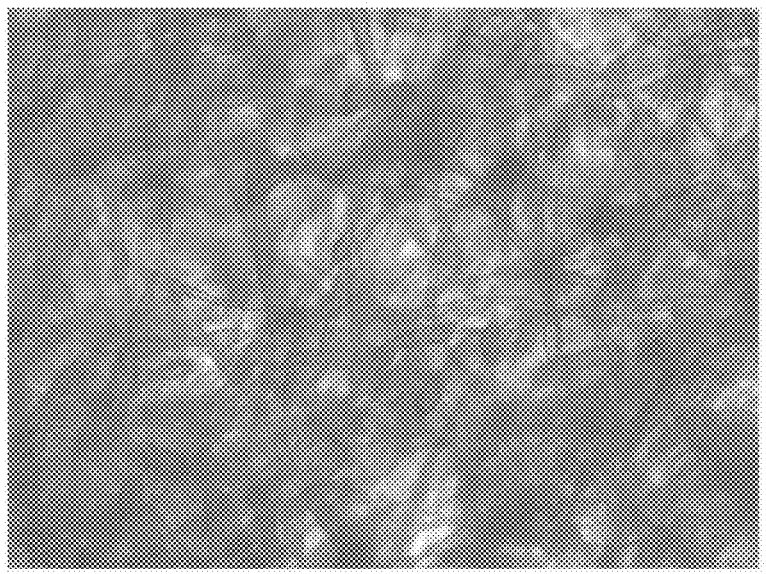

FIGS. 6 and 7 show a control sample of E. coli alone. FIG. 6 is the bright field while FIG. 7 is the FITC filter.

Figure 8:
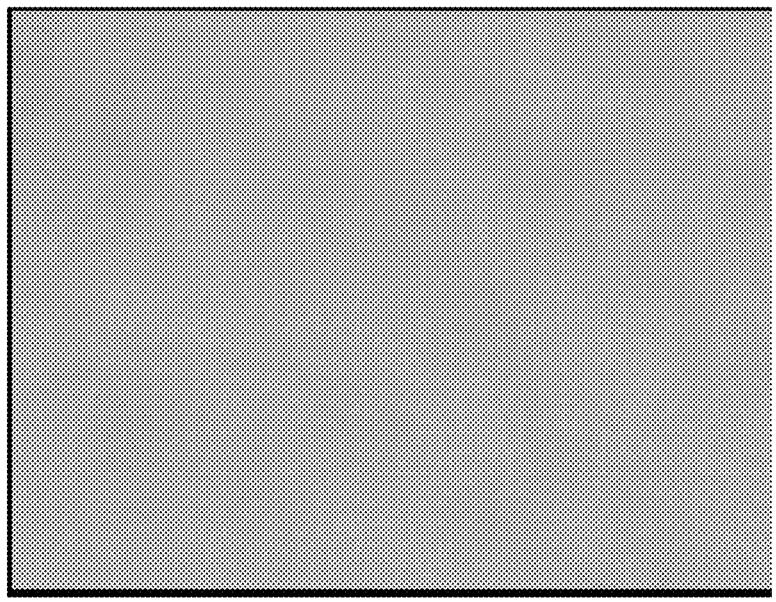
Figure 9:

FIGS. 8 and 9 show the PCL-only material after exposure to E. coli under dark conditions. No stained (i.e. dead) bacteria are seen.

Figure 10:
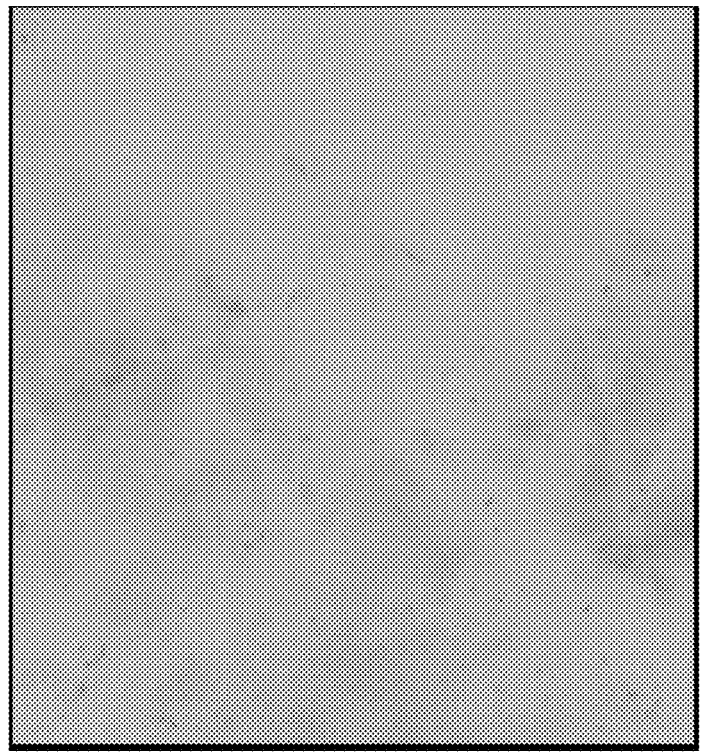
Figure 11:
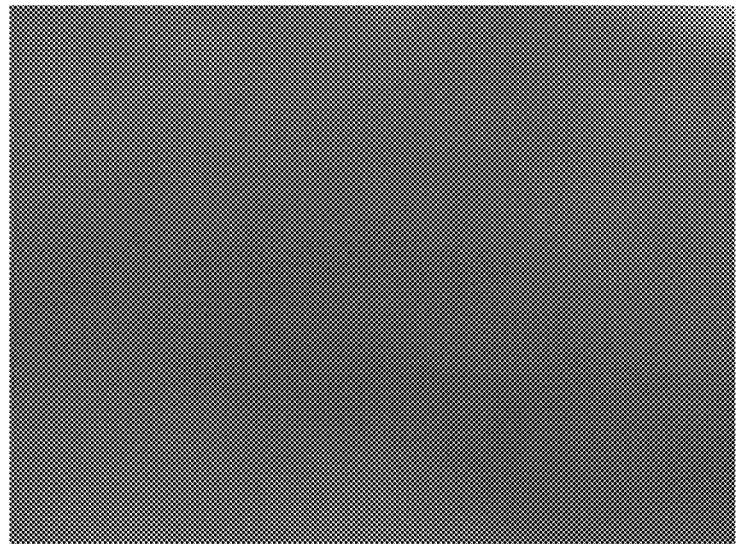

FIGS. 10 (bright field) and 11 (FITC) show the PCL-only material after exposure to E. coli in light conditions. (15 min. under 365 nm @ ~9 mW). It is believed that the few dead E. coli that are seen are due to the light exposure rather than any characteristic of the PCL-only material.

Figure 12:
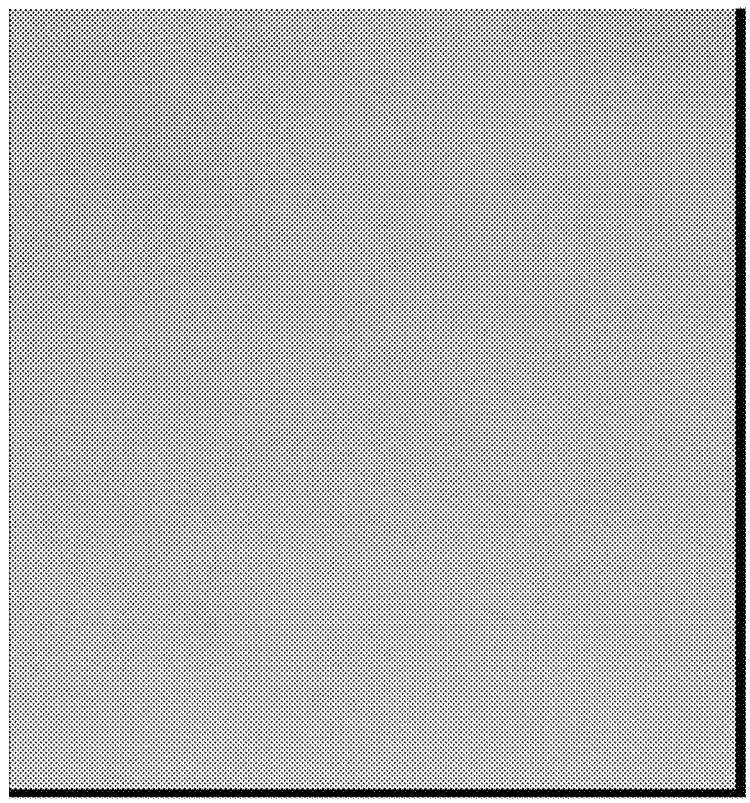
Figure 13:
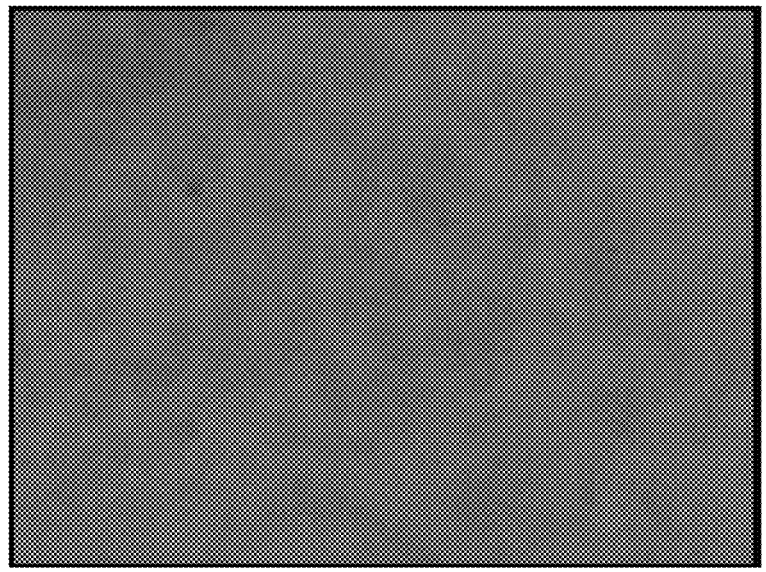
Figure 14:
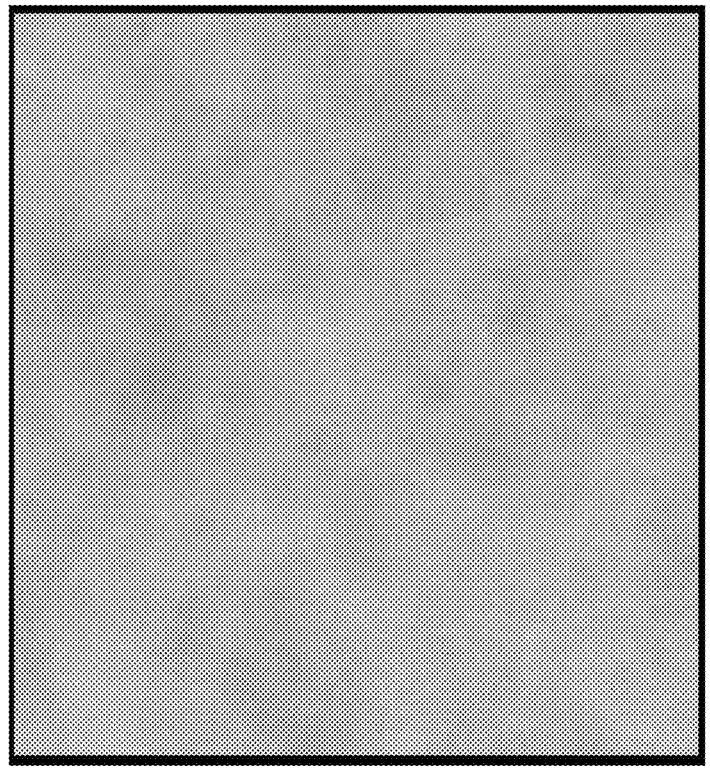
Figure 15:
Figure 16:
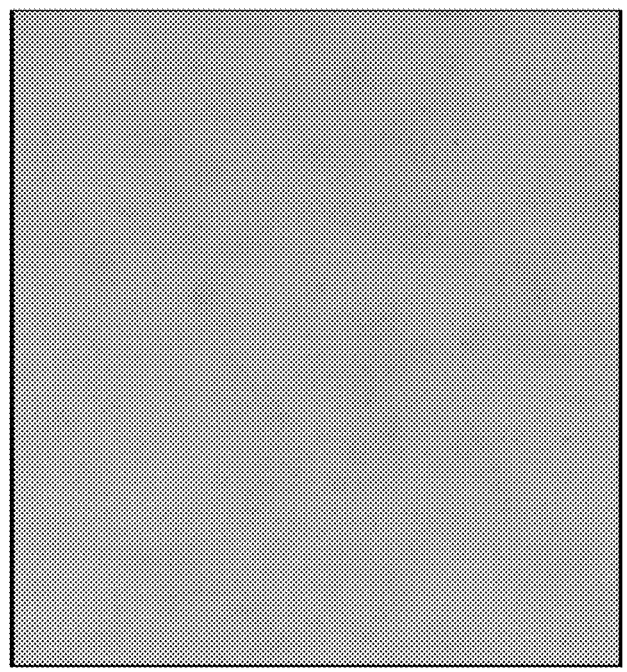
Figure 17:
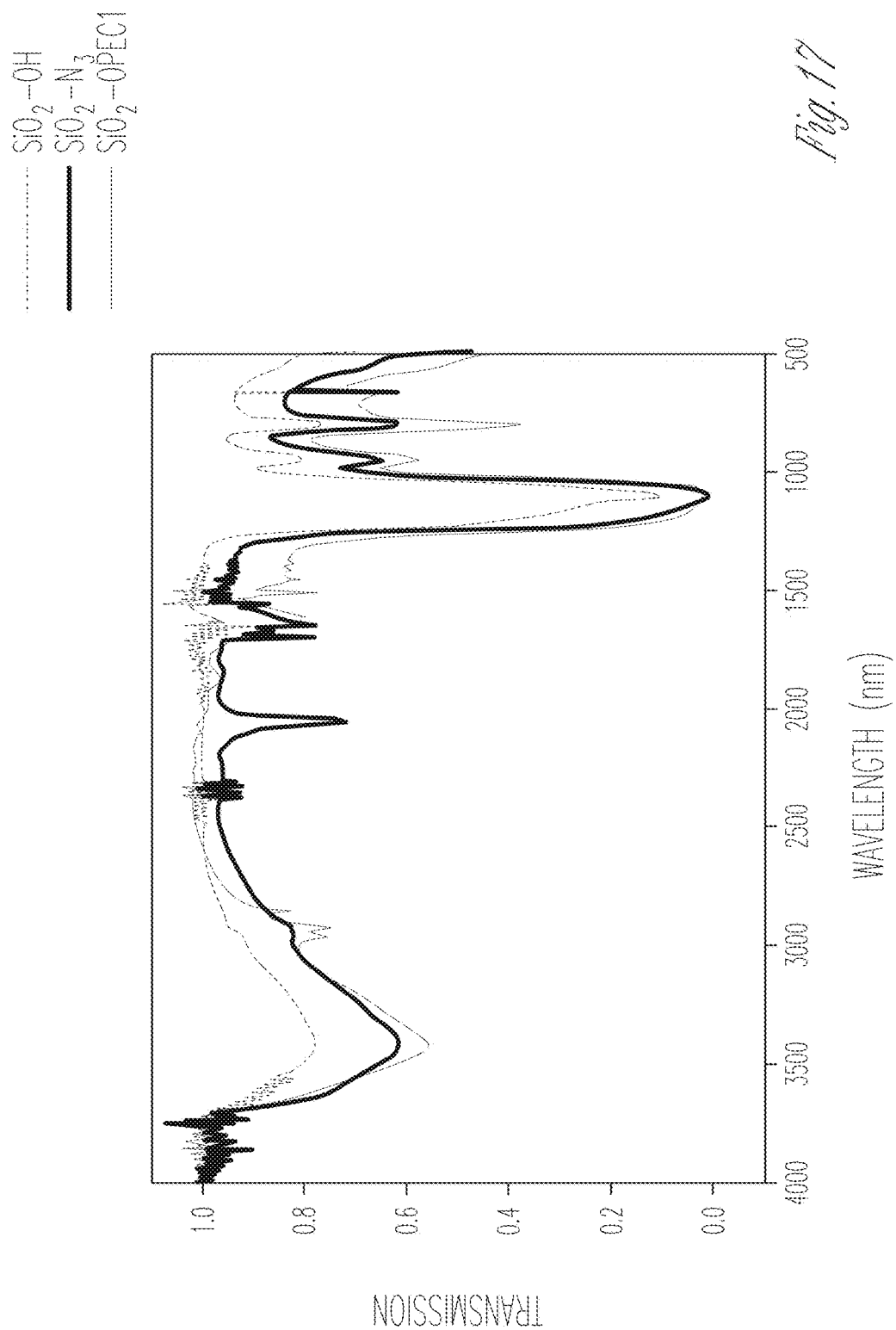

FIGS. 12 (bright field) and 13 (FITC) show the OPE/PCL material after exposure to E. coli in dark conditions. The OPE used in the experiment is generally considered to be a light-activated biocide although, as shown, some activity under dark conditions is observed. FIGS. 14, 15 (bright field) and 16, 17 (FITC) show a very high degree of bacterial capture and kill.

Figure 18:
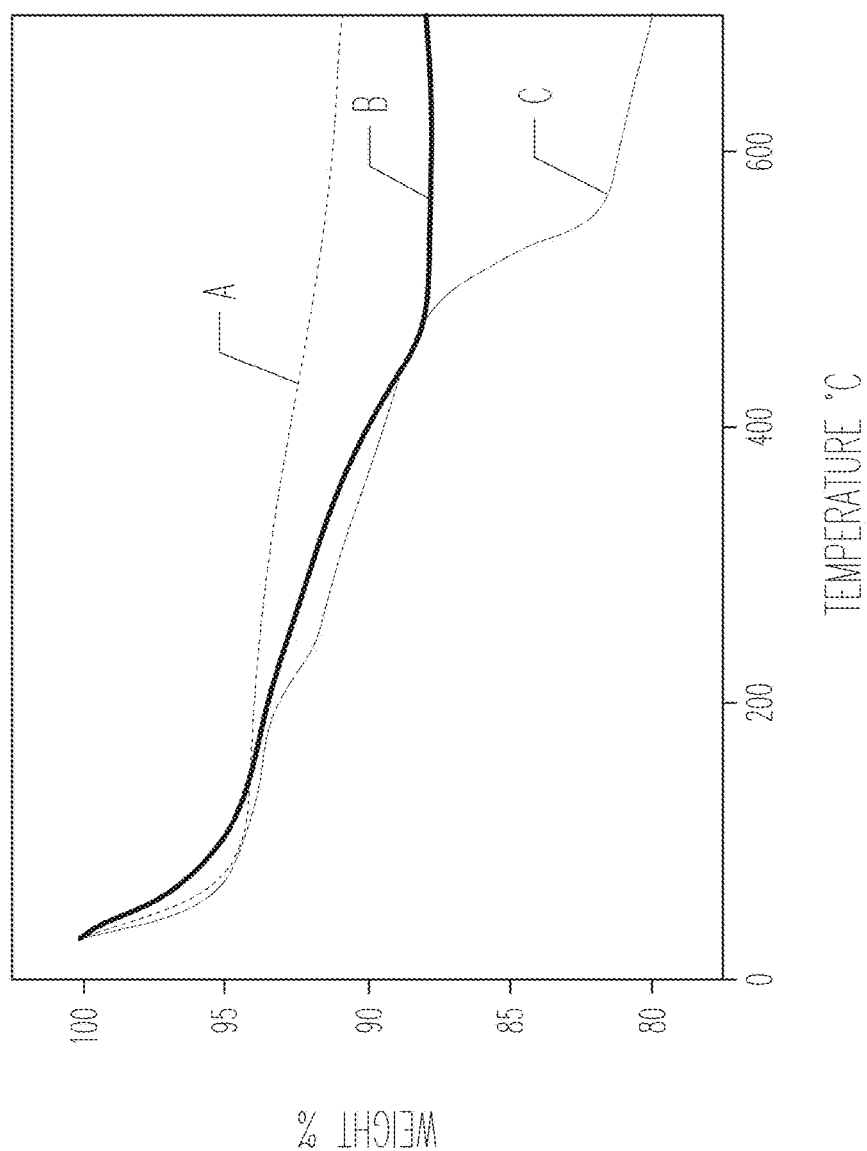

FIG. 18 is a comparison of infrared spectra of silica particles: Unmodified silica particles ($SiO_2$—OH); alkyl azide modified silica particles ($SiO_2$—$N_3$); OPEC1-grafted silica particles ($SiO_2$-OPEC1).

FIG. 19 is a thermogravimetric analysis of silica particles: (a) unmodified silica particles ($SiO_2$—OH); (b) azide-modified silica particles ($SiO_2$—$N_3$); (c) OPEC1-grafted silica particles ($SiO_2$-OPEC1).

FIGS. 20A, 20B, and 20C are Transmission Electron Microscopy images of silica particles: (A) unmodified silica particles; (B) azide-modified silica particles: (C) OPEC1-grafted silica particles.

Figure 21:
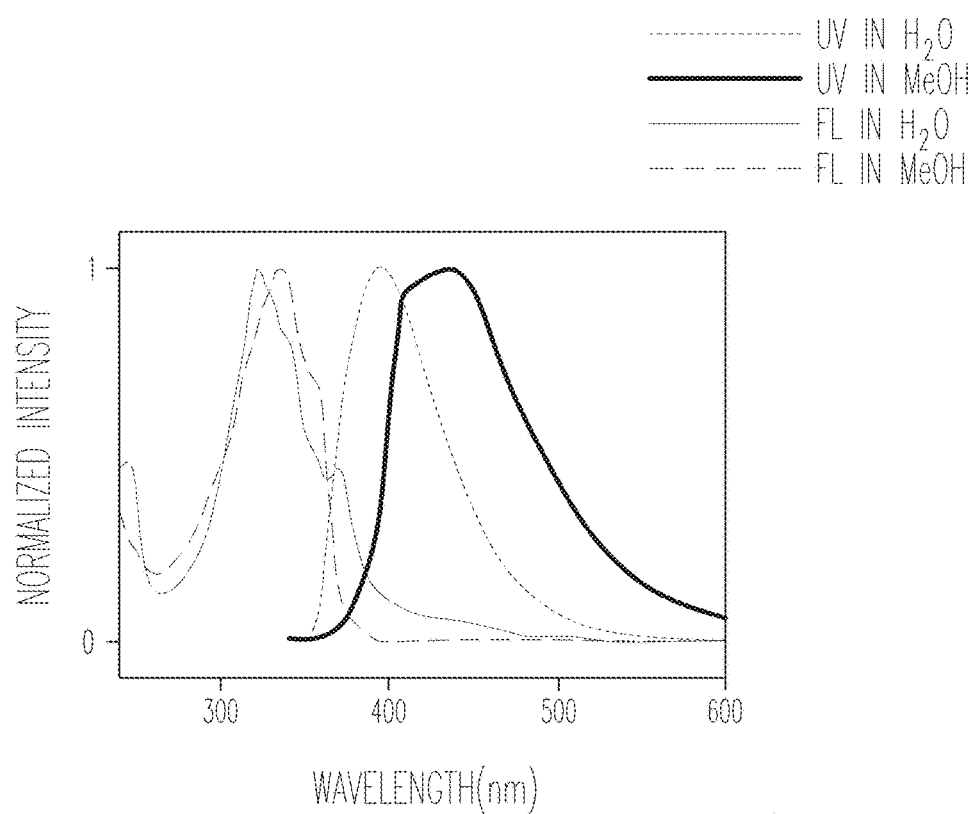

FIGS. 21A, 21B and 21C are Scanning Electron Microscopy images of silica particles: (A) unmodified silica particles; (B) azide-modified silica particles: (C) OPEC1-grafted silica particles.

Figure 22:
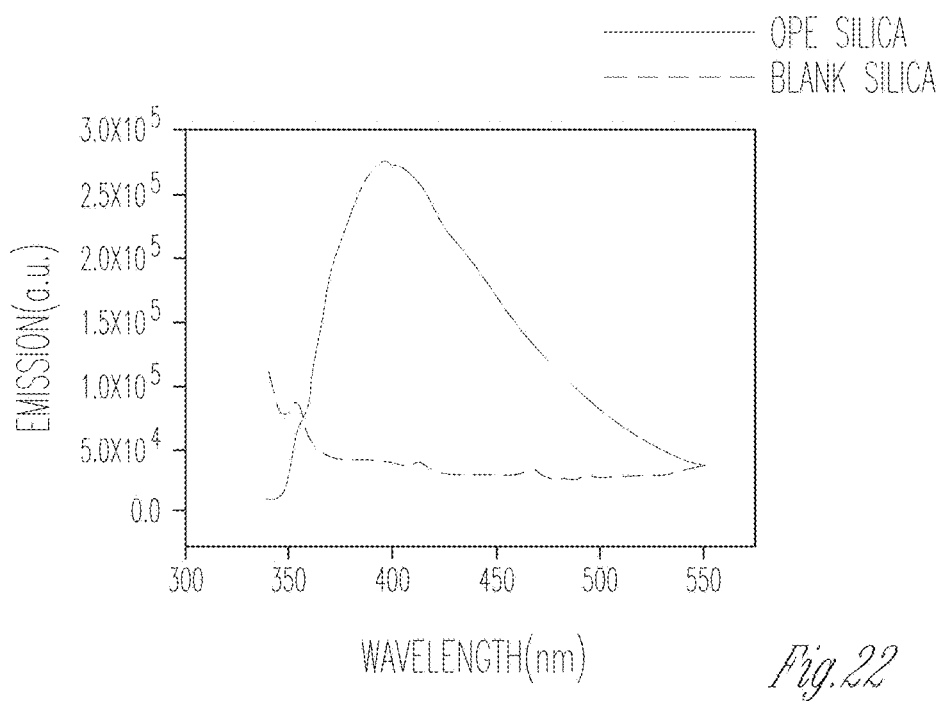

FIG. 22 shows normalized absorption and emission spectra in methanol and water.

Figure 23:
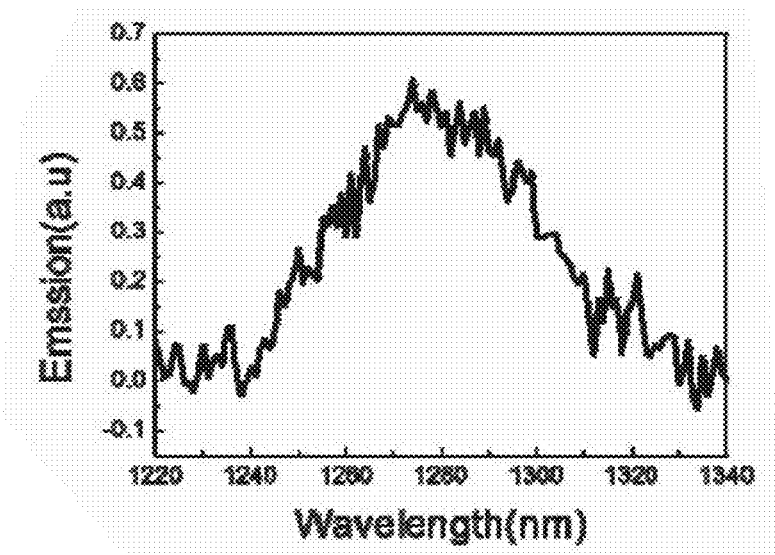

FIG. 23 shows fluorescence spectra of unmodified silica particles and OPEC1-grafted silica particles.

Figure 24:
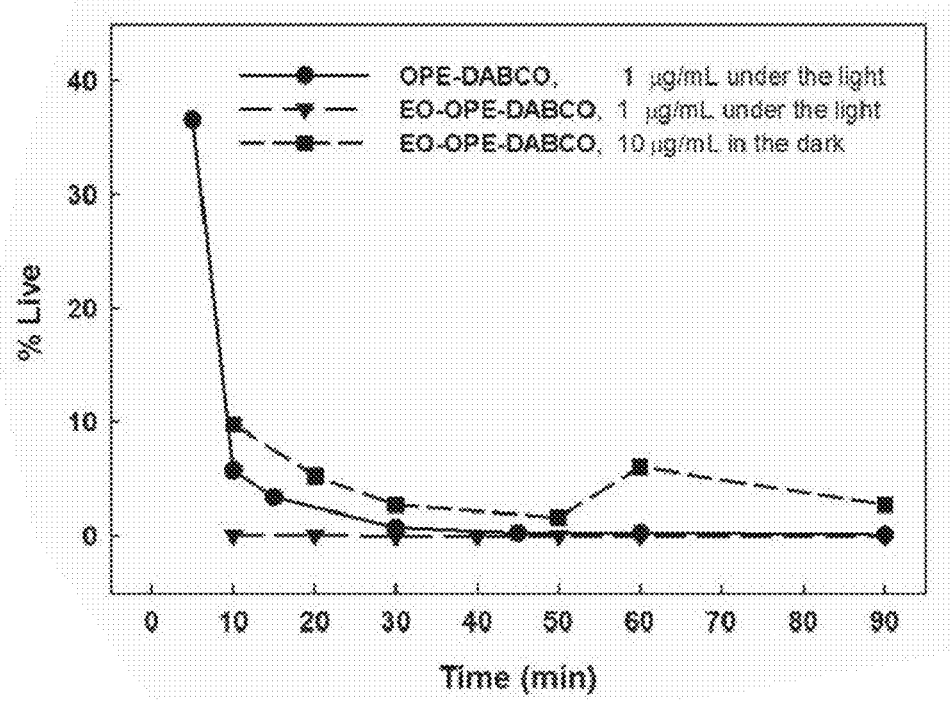

FIG. 24 shows the singlet oxygen spectrum of OPEC1-grafted silica particles in d-methanol.

FIG. 25 is a graph showing the viability of S. aureus cells with 1 µg/mL and 10 µg/mL of OPE-DABCO and EO-OPE-DABCO solution following exposure to UV light and incubation in dark.

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

An "oligomer" as the term is used herein with reference to biocidal oligomers that can be used for decontamination refers to substances with repeating units comprising aryl-ethynyl and/or heteroaryl-ethynyl repeating units, which can be further substituted. The repeating units of the oligomers can be conjugated throughout the molecule, and can absorb visible and/or ultraviolet light. The degree of polymerization (DP) of the oligomers can range from 2, up to several hundred, repeating units. The term "oligomer" is employed for consistency even if some of the higher DP substances could also be termed "polymers". For example, an oligomer used in a method of the invention, can have a DP value of 2, 3, 4, 5, 6, 7, 8, etc., i.e., every counting number above 2 and to an upper limit of about 500, or to an upper limit of about 100, or to an upper limit of about 50, or to an upper limit of about 10. The oligomer chosen by the person of ordinary skill has suitable physical properties, e.g., solubility, extinction coefficient, etc., selected based on the disclosures here in conjunction with ordinary skill.

The expression "effective amount", when used to describe an amount or concentration of a biocidal oligomer, refers to the amount of a biocidal oligomer that is effective to kill or otherwise negatively act on microorganisms such as bacteria or fungi or on quasi-organisms such as viruses that are present in the environment under discussion. For example, an effective amount of a biocidal oligomer in a fiber as disclosed herein is an amount or concentration sufficient to kill microorganism, block their infectivity (e.g., viral particles), inhibit their reproduction (bacteria, fungi) and otherwise act in a manner deleterious to the target organism.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds of the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

With reference to an inventive method of killing bacteria in a biofilm, the term "decontaminating" a surface contaminated with the bacterial biofilm refers to killing the bacteria that make up the biofilm. A surface is "contaminated" with a bacterial biofilm when a biofilm containing living bacteria are disposed on the surface.

A "biocidal" substance, as the term is used herein, refers to a substance that under defined conditions can kill microorganisms, inhibit the growth of individual microorganisms and populations of microorganisms, prevent the establishment of microbial populations, and the like.

The term "in the presence of oxygen" as used herein refers to the presence of molecular oxygen, $O_2$. The oxygen may be present as levels found in air, and the decontamination methods disclosed and claimed herein can be carried out under normal atmospheric conditions.

Biocidal oligomers used in practicing methods of the invention can be of scaffold structure

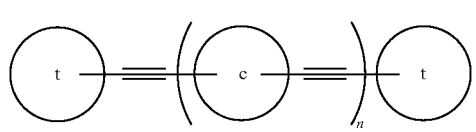

(I)

wherein each circle represents an aryl or heteroaryl ring system, and the rings are joined through conjugate ethynyl (acetylenic) groups, such that the entire scaffold as shown is π-conjugated. The degree of polymerization, n, can be n=1 to about 500, or can be n=1 to about 100, or n=1 to about 50, or n=1 to about 10. Oligomers of this general structural scheme are referred to herein as "poly-(arylene/heteroarylene-ethynylene) oligomers" which are "cationic" when the structure incorporates a positive electrical charge. The person of ordinary skill can select a biocidal oligomer for a particular use based on its physical properties, including solubility (lower molecular weight oligomers can be more soluble in water or in organic solvents), light absorptivity (extinction coefficient at wavelength suitable for decontamination under selected conditions), and reactivity (e.g., for forming covalent conjugates with fiber-forming polymers.

By a "ring system" is meant a monocyclic or polycyclic, substantially planar, aromatic moiety, which can be aryl (carbocyclic) or heteroaryl (containing one or more heteroatoms, e.g., N, O, or S). Examples of an aryl ring system include a monocyclic phenyl ring, or a naphthyl bicyclic moiety. Examples of a heteroaryl ring system include a thienyl (thiophene) monocyclic ring, and a benzothiadiazole bicyclic moiety.

An example of a "cationic" group is a quaternary ammonium group, such as a tetralkylammonium group, which can be cyclic or acyclic, that is covalently bonded to the oligometic scaffold shown above. For example, a group such as $(CH_3)_3N(CH_2)_n$—O—, wherein n is 1, 2, 3, 4, 5, 6, or more, is a cationic group that can be coupled to any available carbon atom in the oligomeric scaffold via the oxygen atom. Alternatively, the oxygen atom shown above can be absent and the cationic group can be bonded directly carbon to carbon; or this moiety can bonded by other groups or atoms as are apparent to the person of ordinary skill. Another example of a cationic group is a "DABCO" group, which as the term is used herein refers to an N-substituted-diazobicyclo-octanyl-N'-alkylene group, such as an N-cyclohexyl-diazobicyclo-octanyl-N'-alkoxy group of formula

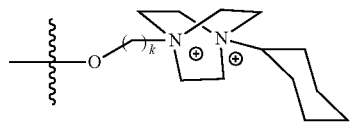

wherein k is 1, 2, 3, 4, 5, 6, or more and a wavy line indicates a point of bonding, charge balanced with two suitable anionic Z⁻ groups such as halide or sulfonate; or an N—(C1-C6)alkyl or an N—(C3-C9)cycloalkyl or an N—(C6-C10) aryl analog thereof; again, this can be bonded to the scaffold through an oxygen atom as shown above, or directly carbon-carbon bonded, or bonded by other groups or atoms as are apparent to the person of ordinary skill. Another DABCO group that can be used as a cationic group in the oligomers used in practice of the inventive methods is an N-cyclohexyl-diazobicyclo-octanyl-N'-alkoxy group. Also, groups other than N-phenyl or N-cyclohexyl can be bonded to the bridgehead nitrogen atom (e.g., N-alkyl groups, other N-cycloalkyl and N-aryl groups) and the bicyclic ring system can be other than a [2.2.2]-bicyclo ring system, as is apparent to a person of skill in the art.

Another example of a cationic group is a sulphonium or a phosphonium group, such as a trialkylsulfonium, a triarylsulfonium, a trialkylphosphonium, or a triarylphosphonium group.

A "fabric" as the term is used herein refers to both woven (such as on a loom) and non-woven (web, mat, etc.) materials that are composed of fibers, which can be a single fiber that is formed into the mat, multiple individual fibers woven into an article or a piece of cloth which can be formed into a garment, mask, and the like. "Fibers" are substantially linear, flexible strands of polymeric materials that can be of various cross-sections, e.g., uniform diameters, varying diameters, films, ribbons, and the like. For example, a fabric, within the meaning herein, could be a mat of a ribbon-like fiber, or a mat of a fiber of circular, polygonal, irregular, or other cross-section. "Non-woven" indicates that the fabric is not formed with a warp and woof configuration on a loom. A "mat" refers to any accumulation of the fiber that creates a pad-like or ribbon-like gauze, i.e. a "web", which can be pressed, made to self-adhere, packaged within a cover, or the like. For example, a mat (web) can be further packaged within coating fabrics or membranes, such as bandage covers, formed from paper, plastic, or any suitable material. A mat can be used as a surgical or wound dressing, as a personal sanitary pad, within a woven garment, or the like. A "woven" fabric can incorporate a fiber having antimicrobial properties prepared by a method of the invention, wherein the fiber is incorporated using a warp and woof technique, as on a loom, to prepare the woven fabric. Both non-woven and woven fabrics manufactured using a biocidal fiber of the invention can incorporate other materials, e.g., other types of fiber, not having antimicrobial properties, such as for fabric strength, texture, color, drape, and the like.

DESCRIPTION

Decontamination of Surfaces Contaminated with Bacterial Biofilms

In various embodiments, the invention provides a method of decontaminating a material contaminated with a bacterial biofilm disposed on a surface thereof, comprising contacting, in the presence of oxygen, the biofilm with an effective amount of a compound of formula (IA)

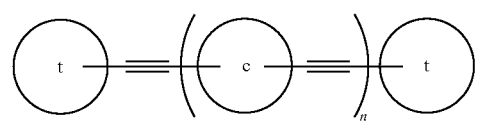

(I)

wherein each circle signifies an aryl or heteroaryl ring system, n=1 to about 100, or n=1 to about 50, or n=1 to about 10, and the compound further comprises one or more moiety comprising an independently selected respective quaternary ammonium cationic group bonded to one or both terminal aryl or heteroaryl ring systems. The effective toxicity of the compound can be enhanced in the presence of light, e.g., visible or ultraviolet light.

The dark and light-induced antimicrobial activity of end-only substituted oligo-(phenylethynylenes) (termed EO-OPEs) containing quaternary ammonium groups has recently been reported.[13,14] It has surprisingly been discovered that the compounds as disclosed herein are highly effective in killing bacteria that are contained within biofilms; biofilms are known to confer resistance on bacteria to the effect of antibiotics. It is believed that the biofilms can serve to block the entry or reduce the effectiveness of typical antibiotics, rendering the bacteria less susceptible to their effect, as described above. Thus, it is unexpected that the EO-OPEs used in the present inventive methods would be highly effective in reaching and killing these protected bacteria. It is believed that a possible mechanism of action, generation of singlet oxygen, may serve to destroy or penetrate the biofilms, due to the small molecular size and highly reactive nature of singlet oxygen.

For example, bacterial biofilms disposed on a surface of a material can be killed or otherwise inactivated using an effective amount or concentration of an "end-only" (EO) cation-derivatized oligomers of formula (IA), examples of which are shown below. It has been unexpectedly discovered by the inventors herein that the "end-only" (EO) forms are significantly more potent in killing bacterial populations residing in biofilms than are other related compounds; i.e., compounds (B)-(E), below, are more potent than is compound (A) for this use. The compounds as shown are charge balanced through the presence of suitable anions, such as halide or sulfonate. The counterions can be bromide, iodide, etc.

Exemplary EO Compounds for Antimicrobial Use Versus Bacterial Biofilms.

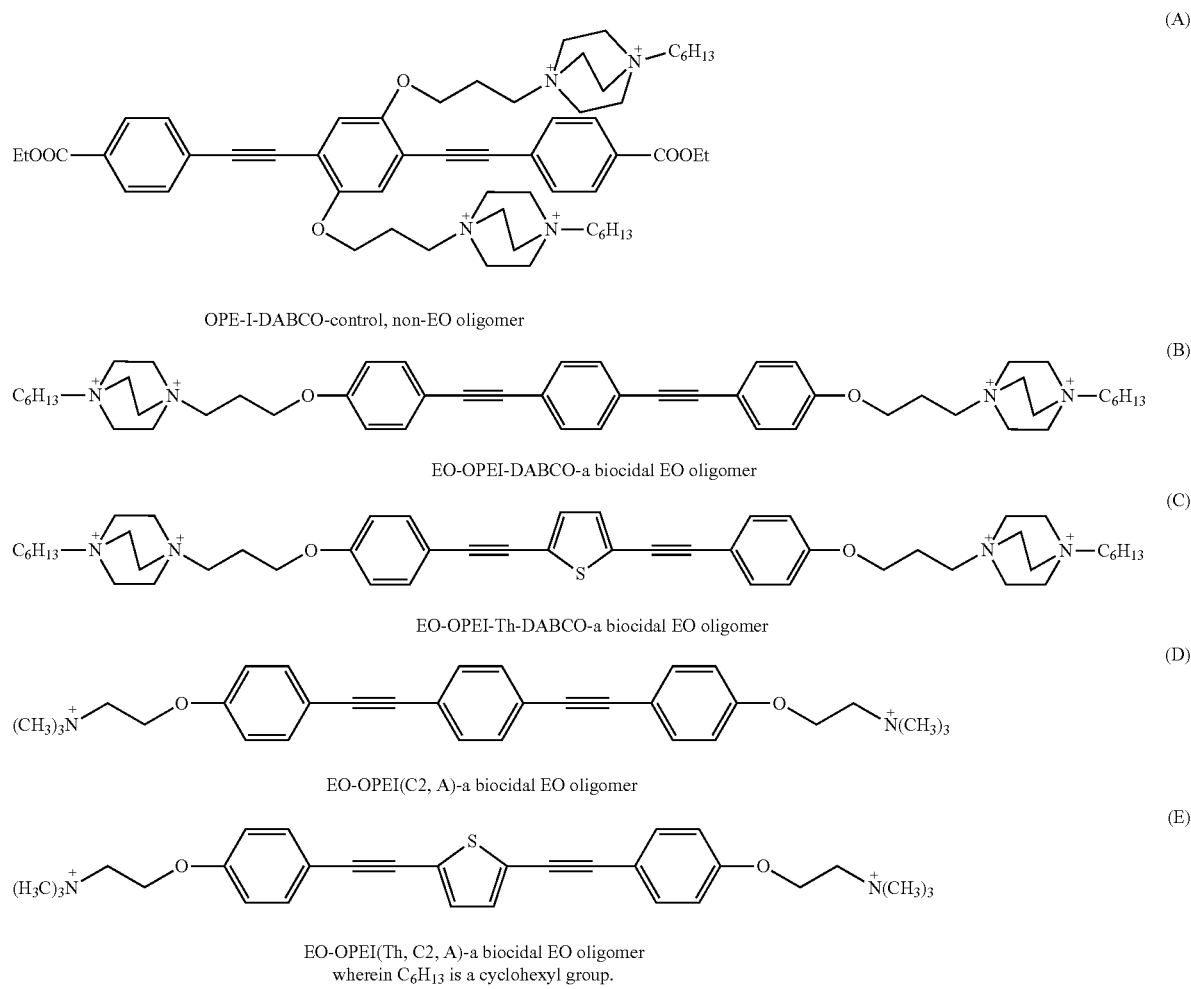

The EO biocidal oligomers exhibit effective toxicity versus bacteria in biofilms at lower concentrations that does a representative control compound (A) that is related to oligomers of formula (I) but wherein the cationic group is bonded to one of the central aryl/heteroaryl ring systems, not to one or both of the terminal ring systems as in the EO oligomers. As noted above, bacteria residing in biofilm populations are often less susceptible to antibiotic action than are planktonic (free-swimming) bacterial, and the enhanced toxicity of the EO cationic poly-(arylene/heteroarylene-ethynylene) oligomers, compared to similar compounds substituted with the cationic groups disposed on non-terminal groups of the oligomers, is surprising and unexpected.

For killing of bacteria in biofilms, it can be desirable to have a high degree of solubility of the biocidal oligomer in water, in an organic solvent such as a water-miscible, non-toxic organic solvent (e.g., ethanol), and the like; accordingly lower n values, that is, lower degrees of polymerization of the oligomer, can provide for materials with greater solubility, which can deliver higher concentrations of biocidal oligomer and hence, it is believed, higher concentrations of singlet oxygen, at the sites where biocidal activity is desired. The person of ordinary skill, using methods disclosed herein in conjunction with ordinary skill, can select optimized parameters for an oligomer of formula (I) for a particular use. Parameters such as the ability to dissolve in a selected solvent medium (water, alcohol, etc.) and the ability to absorb ambient light (daylight, artificial lighting, ultraviolet light) can be altered as needed for a particular situation of use.

Structures and Synthesis

DABCO-containing oligomers ((A), (B), and (C)) were synthesized by Pd-mediated cross-coupling of a terminal arylene and an aryl iodide (Sonogashira coupling). The oligomers were characterized by $^1$H and $^{13}$C NMR. Scheme S1A and S1BC, below, show the overall synthetic approaches to the biocidal oligomers (A), (B), and (C), used in practicing the methods of the invention.

The synthesis of oligomers (D) and (E) was previously reported;[16] Scheme S1DE, below, shows the overall synthetic scheme used in the preparation of compounds (D) and (E). The intermediates bis-ethynylbenzene and bis-ethynylthiophene were prepared by condensation of 1,4-diiodobenzene and 2,5-diiodothiophene, respectively, with trimethylsilylacetylene in the presence of Pd(PPh$_3$)$_2$Cl$_2$, CuI, and diisopropylamine in CHCl$_3$. These precursors were then coupled then quaternized as shown to provide the trimethylammonium species.

Further details concerning the syntheses are provided in the Examples.

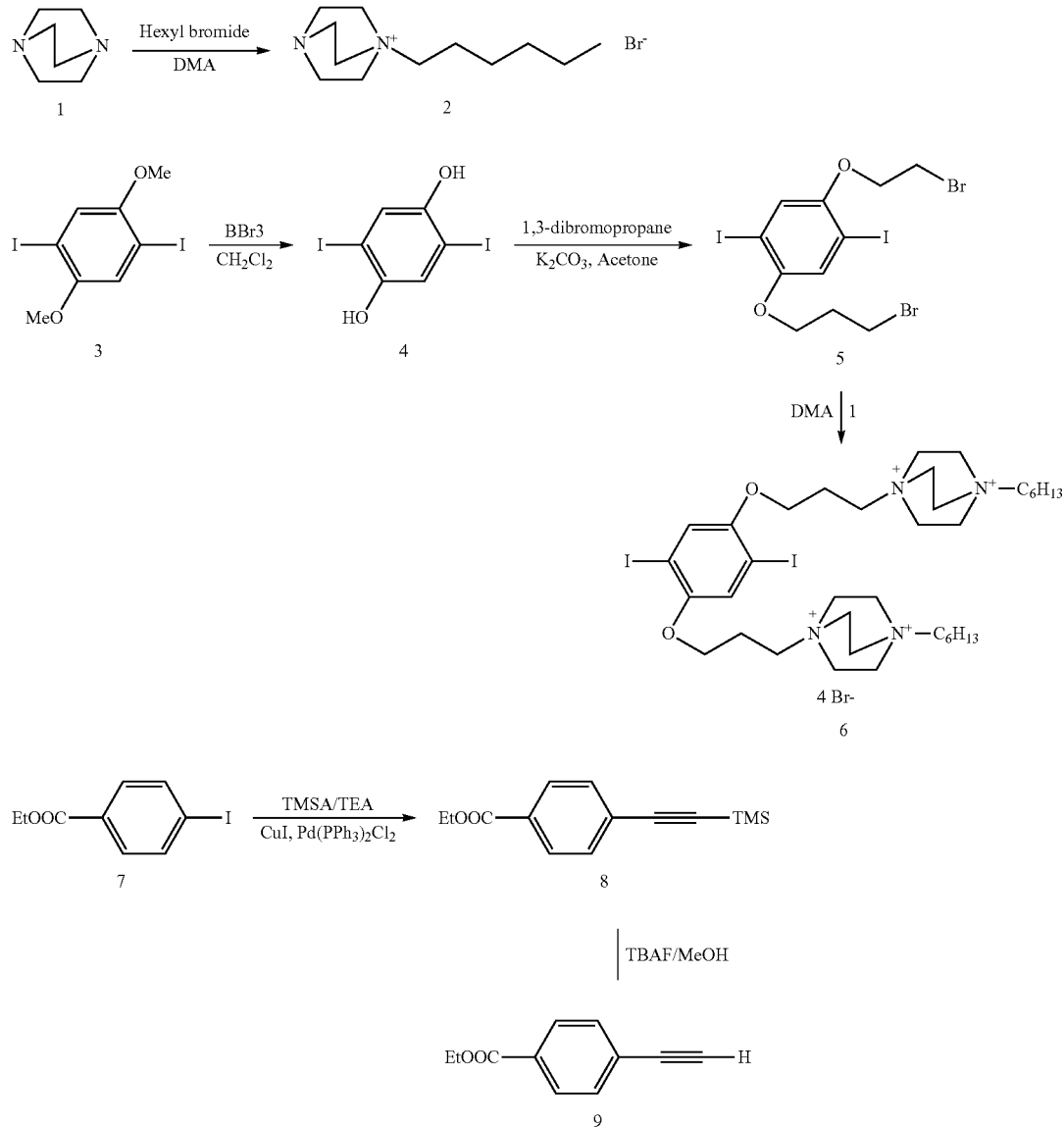

Scheme S1A: Synthetic scheme for oligomer (A)

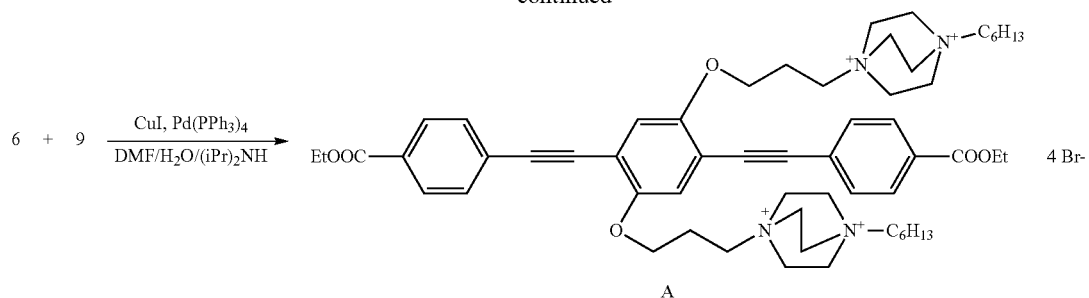
Scheme S1BC: Synthetic scheme for oligomers (B) and (C)
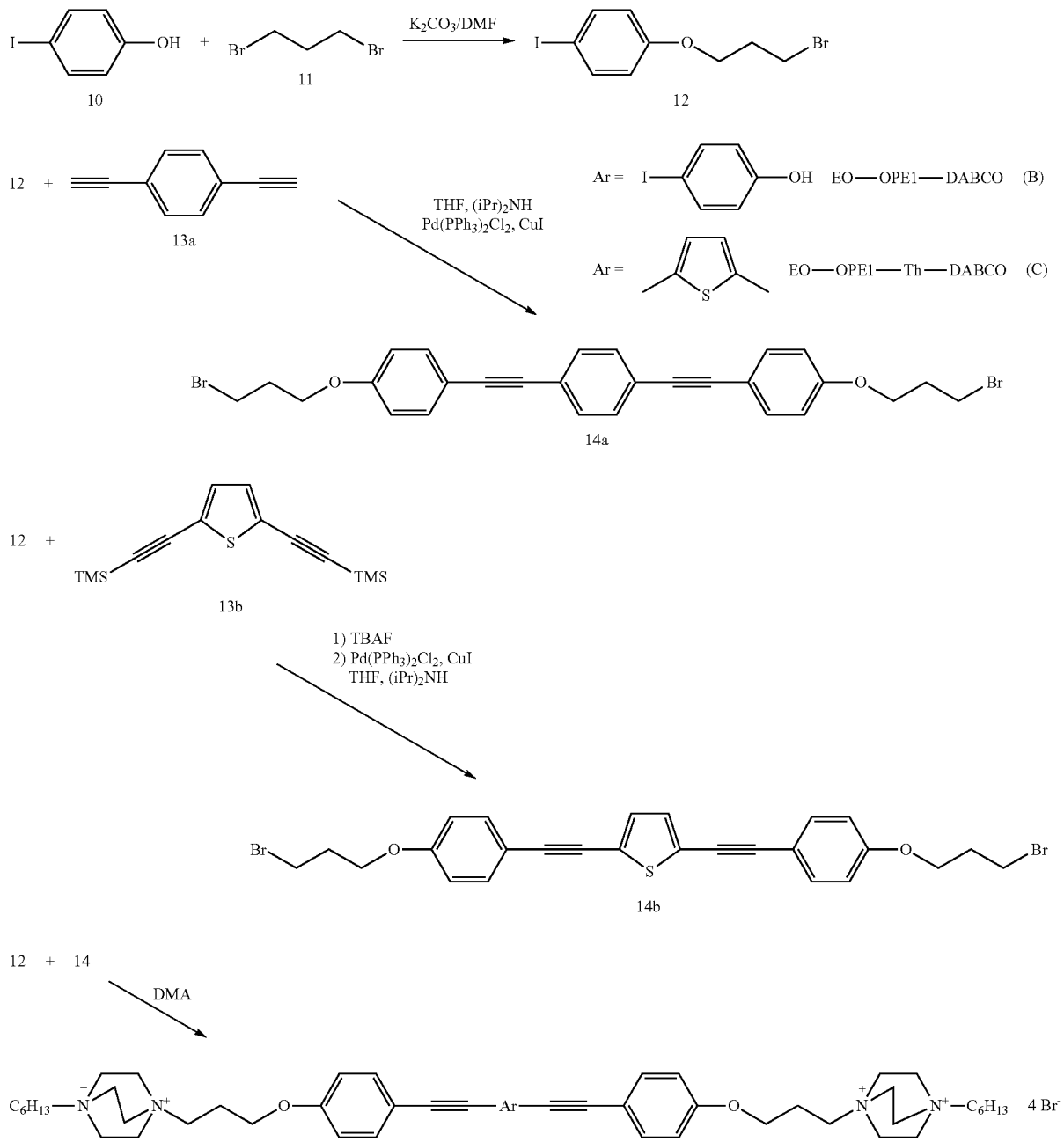

Scheme S1DE: Synthetic scheme for oligomers (D) and (E)

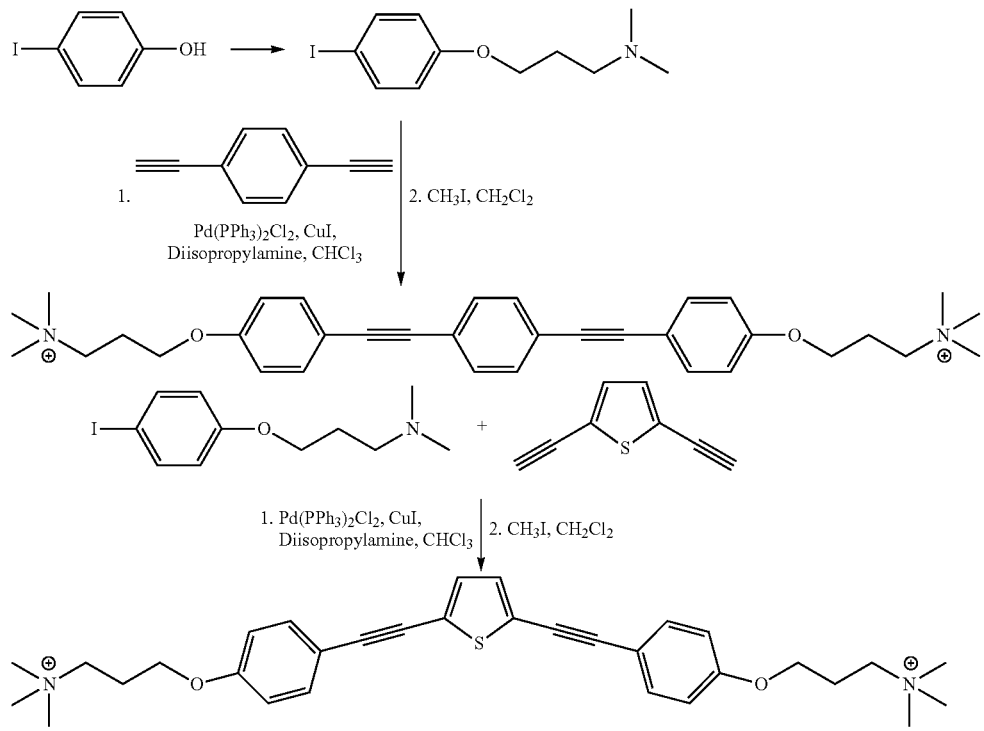

Photophysical Characterization

To gain insight into the light activated biocidal activity of the oligomers, we carried out systematic photophysical studies (Table 1 and supporting information). Comparison of the photophysical data for the oligomers (A)-(E) in methanol solution helps provide a clear understanding of their light activated biocidal action. The oligomers (A)-(E) absorb in the near UV region. Among the end-only oligomers (B)-(E), substituting the center phenylene unit with a 2,5-thienylene unit results in ca 10 nm bathochromic shift in $\lambda_{max}$. Importantly, the oligomers with thienylene units, oligomers (C) and (E), have significantly lower fluorescence quantum yields in methanol solution than the oligomers with phenylene units, oligomers (B) and (D). The fluorescence lifetimes of oligomers (C) and (E) are shorter than those of oligomers (B) and (D). All the above data suggest a rapid deactivation of the singlet state in oligomers (C) and (E) which is consistent with our previous report.[16]

We carried out transient absorption experiments in methanol and water solutions. Consistent with our previous studies, near UV excitation ($\lambda$=355 nm, 5 ns pulse) of the oligomers, (A)-(E), resulted in a transient absorption in the visible region. The lifetime of the transient absorption is in the microsecond range and in each case it is efficiently quenched by $O_2$ indicating the absorption is due to the triplet excited state. By examination of the initial amplitudes of the transient absorption ($\Delta A$, t=0, Table 1), we were able to qualitatively determine the relative triplet yield of these oligomers. Note that the TT absorption ($\Delta A$, t=0) for oligomers with thienylene substitution are significantly larger than the corresponding end-only counterparts with phenylene substitution (i.e., (C)>(B) and (E)>(D)) suggesting a higher triplet yield for the oligomers with thienylene units. As noted before, the fast decay of the singlet excited state in (C) and (E) shows a good correlation with the transient absorption studies and clearly indicates the enhanced rate of intersystem crossing is operative in the oligomers with thienylene units. To substantiate our hypothesis, we carried out studies to observe singlet oxygen emission in deuterated methanol (as the life time of the singlet oxygen is very short in $D_2O$).[21] As anticipated, each of the oligomers is capable of sensitizing the formation of singlet oxygen as observed by its characteristic emission at 1270 nm. Of the oligomers studied, (C) and (E) show a higher quantum yield for singlet oxygen generation ($\Phi_\Delta$) which corroborates well with the photophysical studies described above.

Table 1, below, provides physicochemical data with respect to the biocidal oligomers shown above.

TABLE 1

Photophysical Properties of oligomers in methanol and water

| | Solvent | (A) | (B) | (C) | (D)$^c$ | (E) |
|---|---|---|---|---|---|---|
| $\lambda_{max}^{abs}$ (nm) | MeOH | 366 | 328 | 340 | 326 | 352 |
| | $H_2O$ | 361 | 327 | 340 | 327 | 353 |
| $\lambda_{max}^{fl}$ (nm) | MeOH | 427 | 357 | 391 | 358 | 388 |
| | $H_2O$ | 465 | 390 | 412 | 388 | 409 |

TABLE 1-continued

Photophysical Properties of oligomers in methanol and water

| | Solvent | (A) | (B) | (C) | (D)[c] | (E) |
|---|---|---|---|---|---|---|
| $\Phi_{fl}$[a] | MeOH | 0.51 ± 0.02 | 0.60 ± 0.02 | 0.11 ± 0.02 | 0.69 ± 0.03 | 0.18 ± 0.02 |
| | H$_2$O | 0.03 ± 0.02 | 0.34 ± 0.02 | 0.07 ± 0.02 | 0.44 ± 0.02 | 0.14 ± 0.02 |
| $\tau_{fl}$ (ns) | MeOH | 1.44 (450) | 0.42 (400) | 0.24 (420) | 0.45 (400) | 0.23 (420) |
| | H$_2$O | 0.14 (450) | 0.59 (90%), 0.05 (10%) (400) | 0.20 (420) | 0.52 (400) | 0.18 (420) |
| triplet abs | MeOH | 0.34 | 0.14 | 0.32 | 0.28 | 0.42 |
| ($\Delta$A, t = 0) | H$_2$O | 0.01 | 0.08 | 0.15 | 0.07 | 0.26 |
| $\tau_{triplet}$ (µs) | MeOH | 3.7 | 2.7 | 3.0 | 2.3 | 3.2 |
| | H$_2$O | — | 8.5 | 35.7 | 18.7 | 13.1 |
| $\Phi_\Delta$[b] | CD$_3$OD | 0.34 ± 0.03 | 0.20 ± 0.02 | 0.46 ± 0.02 | 0.17 ± 0.03 | 0.64 ± 0.03 |

[a]Measured using quinine sulfate in 0.1M sulfuric acid ($\Phi_F$ = 0.54) as an actinometer.
[b]Measured in CD$_3$OD using 2'-acetonaphthone ($\Phi_\Delta$ = 0.79) as an actinometer.
[c]Reference 16
[d](nm)

To screen the effectiveness of EO-OPEs shown above at killing bacteria residing in a biofilm, a Calgary Biofilm Device (CBD), commercially available as the MBEC™ assay was used to grow 96 equivalent biofilms at a time, and to determine the minimum inhibitory concentration (MIC). After incubating the CBD devise in *Escherichia coli* (*E. coli* K12) suspension in LB media for 24 hours, biofilms were uniformly formed on the CBD surface. The *E. coli* biofilms were then incubated with EO-OPEs for 24 hours to obtain their MIC values.

Table 2, below, shows the antimicrobial minimum inhibitory concentration (MIC) values of the four EO compounds shown above, compared with the MIC values of compound OPE-1-DABCO and of the known antibiotic kanamycin.

TABLE 2

Sensitivity of *E. coli* biofilm bacteria to antimicrobial oligomers (µg/mL).

| | (A) | (B) | (C) | (D) | (E) | kanamycin |
|---|---|---|---|---|---|---|
| MIC | 51.7 | 14.0 | 15.8 | 34.0 | 32.7 | 11.2 |
| MBEC (dark) | >1000 | 200 | 150 | 200 | >1000 | >1000 |
| MBEC (light) | >500 | 60 | 60 | 70 | 200 | — |

The heightened potency of the EO compounds of formula (I), oligomers (B)-(E), versus a related control compound (A) wherein the cationic group is not bonded to a terminal aryl/heteroaryl ring system, is shown from comparative results obtained from testing EO compound EO-OPE-1-DABCO, which provides 90% inhibition of *E. coli* K12 in the biofilm at a concentration of 14 µg/mL, versus 52 µg/mL for a related oligomer (A) comprising the same N-phenyl-DABCO-alkoxy substituent but wherein the substituent is bonded to a non-terminal aryl/heteroaryl ring system. Killing efficiency was determined by measurement of the optical density at 600 nm wavelength.

The inventors herein believe that light-induced biocidal activity of EO-OPEs correlates with their relative triplet yields and a higher triplet yield affords better light-induced biocidal activity. It has also been shown that EO-OPEs show interactions with dioleoyl-sn-glycero-3-phosphocholine (DOPC)/cholesterol vesicles. Therefore, the inventors herein believe that biocidal action involves the following steps: (1) EO-OPEs penetrate the bacterial membrane, (2) EO-OPEs photosensitize the generation of singlet oxygen, and (3) singlet oxygen and/or reactive oxygen species trigger bacterial death.[16] The bacterial cells growing in biofilms feature slow growth rates and higher resistance to antimicrobials.

EO-OPE-DABCO compounds were found to inhibit the propagation of *E. coli* biofilms (detachment of bacteria from the surface of the biofilm to the liquid medium followed by regrowth) at concentration level similar to the concentration of known antibiotic kanamycin. The incorporation of the DABCO group into the EO-OPEs is believed to enhance their diffusion into the cell wall due to similarities of the pendent group and the lipid layer. It was also found that EO-OPE-DABCO compounds were effective in killing biofilm bacteria in the dark at relatively low concentrations, as well as after 3 hr exposure to white light.

See also: Z. Zhou, et al., DOI: 10.1021/jz101088k *J. Phys. Chem. Lett.* 2010, 1, 3207-3212; Y. Tang, et al., dx.doi.org/10.1021/la105018g|Langmuir 2011, 27, 4956-4962; D. Whitten, et al., DOI: 10.1021/la302476s•Publication Date (Web): 16 Jul. 2012; the disclosures of which are incorporated herein by reference in their entireties.

Decontamination and Prevention of Contamination of Fabrics

In uses where bacterial contamination of objects and materials in the environment represents a serious medical and public health concern; such as in treatment of patients prone to infections, e.g., with wounds, compromised immune systems, in pediatric and geriatric care, during and following surgery, and the like; in food preparation and handling wherein bacterial contamination of foodstuffs, work surfaces, tools and appliances, and food workers themselves, can and does present an often lethal threat of food poisoning; in treatment of drinking water supplies; and in consumer personal hygiene products; decontamination and prevention of contamination of physical objects can be critical. Above, the use of biocidal oligomers for the decontamination of generally non-porous surfaces by the use of biocidal oligomers such as the cationic oligo-(arylene/heteroarylene-ethynylene) oligomers, in the presence of oxygen (e.g., in air), and optionally under illumination by light, is described as a method of killing bacteria and controlling bacterial populations when the bacteria are growing within protective biofilms they secrete on surfaces. In addition to such types of surfaces on which bacterial biofilms are prone to contaminate, porous materials such as fabrics can harbor populations of pathogenic bacteria.

Fabrics, comprising multitudes of individual fibers, provide many occluded spaces in which bacterial populations can thrive that are not readily accessible to sterilizing agents. For example, such refuges can be shielded from UV light, often used to kill bacteria in medical and in food preparation environments. Accordingly, use of inventive methods as described herein to decontaminate fabrics, such as non-woven materials, as well as to inhibit the establishment of bacterial populations in such materials in the first place, provides a benefit of reducing the chance of infection. For example, in many uses fabrics may be sterile when first used, but soon become contaminated with biological materials that support and stimulate bacterial growth. Examples include wound dressings, surgical garments, absorbents, personal hygiene products, and the like. Even garments not used in a sterile or protected setting can benefit from inclusion of antimicrobial fabric components, e.g., in keeping garments free from bacterially induced odor. In various embodiments, the present invention discloses and claims methods and materials that can accomplish these goals by providing various embodiments of fabrics, such as non-woven fabrics, that block establishment of microbial colonies and kill microorganisms that invade the substance.

According to an embodiment the present disclosure provides a non-woven fibrous mat incorporating an antimicrobial agent and methods for forming and using the mat in various applications where inhibition of bacterial growth is desired. The fibrous material can be formed by combining a fiber-forming polymer and one or more biocidal oligomer such as a cationic oligo-(arylene/heteroarylene-ethynylene) oligomer, to produce fibers that can be formed into a continuous sheet of non-woven material. The composition comprising the fiber-forming polymer and the one or more biocidal oligomer can be formed into a fiber form by any suitable method of fiber spinning known to the person of skill. Alternatively, an existing fiber composition can be treated with a suitable preparation of a biocidal oligomer to provide the fiber containing the antimicrobial material; in various embodiments, the oligomer can be non-covalently associated with the polymer, e.g., by association of the cationic oligomer with a cellulosic fiber (e.g., cotton, rayon), as cationic substances are known to adhere to negatively charged cellulose microfibrils; or by association of the cationic oligomer with an anionic polymeric material such as an alginate (containing carboxylic acid groups). In other embodiments, the biocidal oligomeric materials can be covalently linked to either a synthetic fiber-forming polymer, which can then be spun by any suitable method; or to a natural fiber composed, e.g., of cellulose, alginates, gelatin, chitosan, or the like, using methods, e.g., of "click" chemistry. For instance, a biocidal oligomer containing a terminal ethynyl group can be covalently bonded to a natural fiber such as cellulose that has been modified to include azido groups, by using the acetylene-azide click reaction, that forms linking triazole groups to bond the oligomer to the fiber material, as described in greater detail below.

For spinnable fiber-forming polymers, while the presently described method is explained primarily in connection with electrospinning (see, for example, Leach, M. K., Feng, Z., Tuck, S. J., Corey, J. M. Electrospinning Fundamentals: Optimizing Solution and Apparatus Parameters. *J. Vis. Exp.* (47), e2494, DOI: 10.3791/2494 (2011); An Introduction To Electrospinning And Nanofibers, Seeram Ramakrishna, ISBN: 978-981-256-454-2), it will be understood that the presently described method is applicable for use with a wide variety of other textile formation techniques well known in the art including, but not limited to, meltblowing, melt spinning, dry spinning, wet sinning, gel spinning, single head electrospinning, multihead electrospinning, or flash spinning. Furthermore, the method is applicable for use with all spinning techniques with or without a method to preferentially orient the fibers, including, but not limited to methods that include the use of a mandrel. The method is also applicable for use with all spinning techniques with or without a method to decrease the fiber diameter, including, but limited to methods that incorporate stretching.

Fiber-forming polymers used can be polycaprolactone (PCL), poly-alpha-hydroxyesters, e.g., poly-lactic-glycolic acid (PLGA), poly-lactic acid (PLA), poly-glycolic acid (PGA), other aliphatic polyesters such as glycol-type polyesters of dibasic aliphatic diacids, aromatic polyesters such as glycol-type polyesters of dibasic aromatic acids (terephthalate, etc.) polyvinyl alcohol (PVA), polyethylene oxide (PEO), or polyolefins such as polyethylene, polypropylene, polyethylene/polypropylene copolymers, polystyrene (PS), and the like; or the fiber-forming polymers can be natural materials such as cellulose, chitosan, alginate, gelatin, and the like. Some of the polymers can be spun with the biocidal oligomers present, or can be treated post-spinning; other fibers not suitable for spinning (e.g., cellulose, although cellulose can be spun as a derivative, e.g., viscose, then regenerated), can be treated with the biocidal oligomers as preformed fibers.

In various embodiments, the biocidal oligomers can be a cationic oligo-(arylene/heteroarylene-ethynylene), such as the variously termed poly(phenylene ethynylene) (PPE)-based cationic conjugated polyelectrolytes (CPEs), cationic phenylene ethynylene oligomers (OPEs), and conjugated polyampholytes as described in PCT patent application nos. PCT/US2009/048838, PCT/US11/43908, PCT/US11/43922, U.S. patent application Ser. No. 13/001,478, and U.S. provisional patent application No. 61/422,130 (each of which is hereby incorporated by reference in its entirety). These cited documents disclose a variety of suitable oligomers and polymers that exhibit dark and light-activated biocidal activity against Gram positive and Gram negative bacteria and bacterial spores. Furthermore, as described in the above-incorporated references, some of the oligomers and polymers possess anti-viral and/or anti-fungal properties as well. Such oligomers can be incorporated into fibers by methods disclosed and claimed herein, to provide biocidal fabrics for various uses, e.g., medical, food preparation, personal hygiene, and any others where control of microbial populations is desired.

Various oligomeric compounds that can be used in the preparation of fibers and non-woven mats or webs of the invention include those as shown below:

1) An oligomer of formula (F)

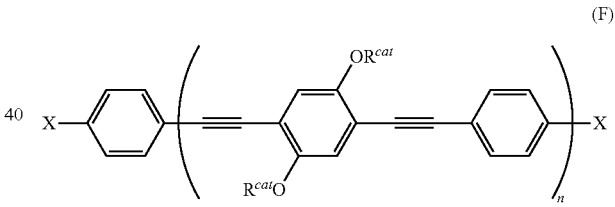

(F)

wherein X is independently H, CO2R, C(=O)R, NR2, or C≡C—R, wherein one or more X groups can be bonded at any available position(s), R is independently H or (C1-C6) alkyl, n is 1 to about 10, and $R^{cat}$ is a cationic group. X can also be a cationic group in various embodiments.

For example, $R^{cat}$ can be $-(CH_2)_3N^+(R^1)_3$, wherein each $R^1$ is independently (C1-C6)alkyl; or two $R^1$ together with the nitrogen atom to which they are bonded form a 3-9 membered heterocyclyl optionally comprising 1-3 additional heteroatoms selected from NR, O, and S(O)q wherein q=0, 1, or 2; or three $R^1$ together with the nitrogen atom to which they are bonded form a 4-12 membered bicyclic heterocyclyl optionally comprising 1-3 additional heteroatoms selected from NR, O, and S(O)q wherein q=0, 1, or 2; or, $R^{cat}$ can be a group of formula

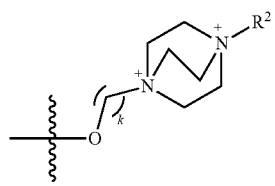

wherein k=1, 2, 3, 4, 5, 6, or more, $R^2$ is (C1-C6)alkyl, (C1-C6)alkoxy, (C3-C9)cycloalkyl, (C3-C9)cycloalkoxy, or aryl, and a wavy line indicates a point of bonding.

Or the oligomer can be
2) an oligomer of formula (G)

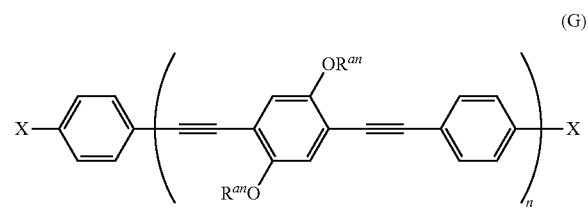

(G)

wherein X and n can be as defined for the oligomer of formula (F), and $R^{an}$ comprises an anionic group, provided that at least one X is a cationic group, such that the oligomer comprises at least one cationic group, wherein one or more X groups can be bonded at any available position(s). For example, $R^{an}$ can be a group of formula $-O(CH_2)_kSO_3^-$, wherein k=1, 2, 3, 4, 5, 6, or more.

Or the oligomer can be
3) an oligomer of formula (H)

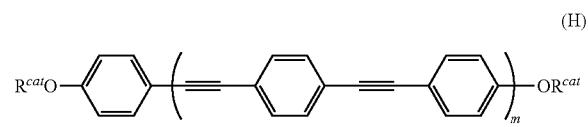

(H)

wherein each independently selected $R^{cat}$ is as defined for the oligomer of formula (F), wherein one or more X groups can be bonded at any available position(s), and m=1 to about 10.

Or the oligomer can be
4) an oligomer of formula (J)

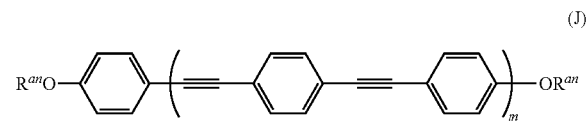

(J)

wherein m is as defined for formula (H), wherein one or more X groups can be bonded at any available position(s), and $R^{an}$ comprises an anionic group. For example, $R^{an}$ can be a group of formula $-O(CH_2)_kSO_3^-$, wherein k=1, 2, 3, 4, 5, 6, or more; but provided that at least one ring is substituted with a cationic group, such that the oligomer comprises at least one cationic group. In any compound of formulas (F), (G), (H), and (J), one or more independently selected X group(s) are optionally bonded at any available position; i.e., there can be 0, 1, 2, 3, 4, or more independently selected X groups present in any of formulas (F), (G), (H), or (J).

In any of the above formulas (F), (G), (H), and (J), any of the aryl ring systems, shown as phenyl rings, can be replaced with a heteroaryl ring system, such as a thienyl ring. Also, in any of the above formulas, any of the aryl or heteroaryl ring systems can bear additional substituents, such as hydroxyl, amino, thio, acyl, alkyl, alkoxy, acryloyl, activated ester, and the like. The substituents can be selected for reactivity with a complementary reactive group on the polymer when it is desired to covalently couple the oligomer and the polymer, such as by electrophile-nucleophile reactions, cycloaddition reactions, or other coupling reactions such as are known in the art.

In various embodiments, the oligomer can be any of formulas (H1), or (J1), below, wherein each EO scaffold bears respectively only a single cationic or anionic group at one terminal aryl/heteroaryl ring system, and the other terminal ring system can be unsubstituted or can be substituted with j=1, 2, 3, 4, or 5 J groups such as hydroxyl, amino, thio, (C1-C6)alkyl, (C1-C6)acyl, (C1-C6)alkoxy, (C3-C9)cycloalkyl, (C3-C9)cycloalkoxy, or aryl; but provided that each oligomer contains at least one cationic group.

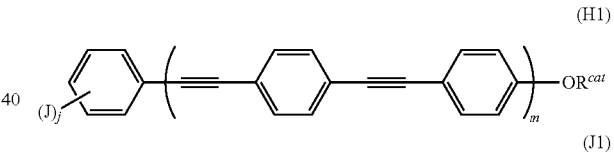

In more specific embodiments, the oligomer incorporated with the fiber-forming polymer prior to spinning, or associated with a fiber spun or natural, can be any of the following:

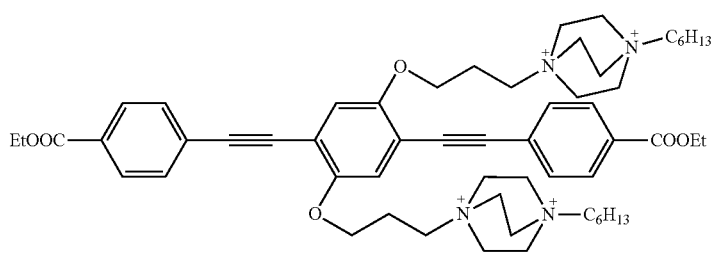

OPE-I-DABCO-control, non-EO biocidal oligomer

-continued

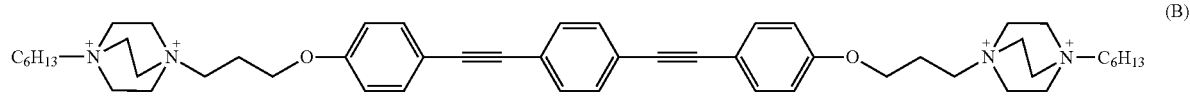
EO-OPEI-DABCO-an EO oligomer (B)

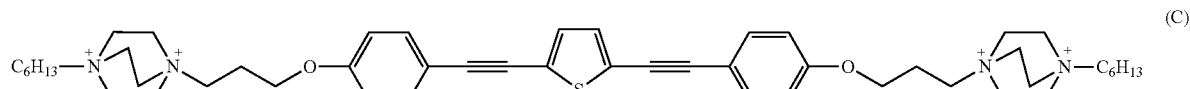
EO-OPEI-Th-DABCO-an EO oligomer (C)

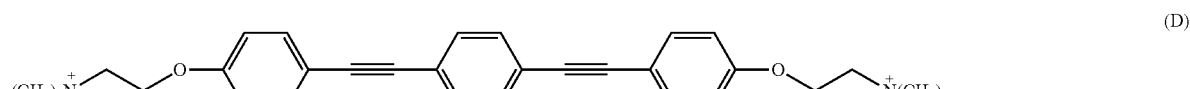
EO-OPEI(C2, A)-an EO oligomer (D)

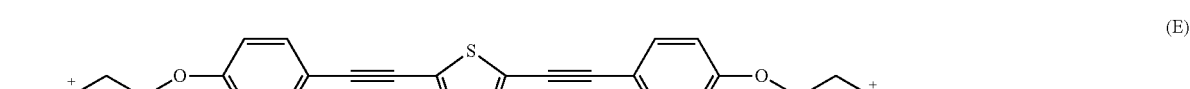
EO-OPEI (Th, C2, A-an EO oligomer (E)

Some examples include oligomers of the following structures:

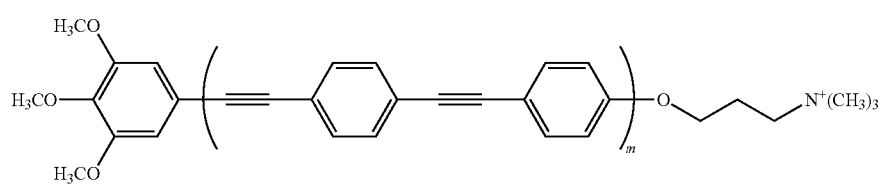

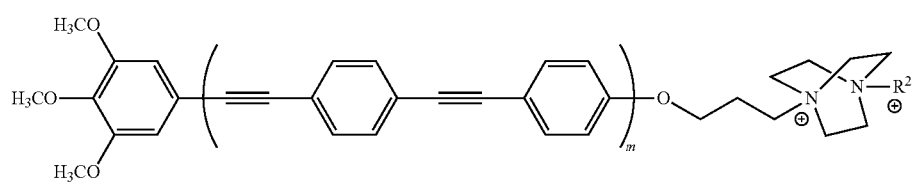

wherein $R^2$ is alkyl, phenyl, cyclohexyl, or the like, and m=1 to 10, or 1 to 50, or 1 to 100, or 1 to 500.

In other embodiments, oligomers, which can have a degree of polymerization (DP) from about 2 up to 20, or up to 50, or up to 100, or more, repeating units of the general formula

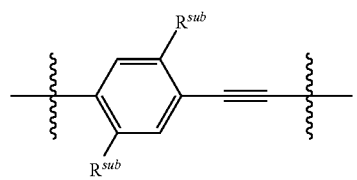

wherein the wavy lines indicate points of bonding to other similar repeating units, can include in regular or random sequence repeating units of any of the following formulas:

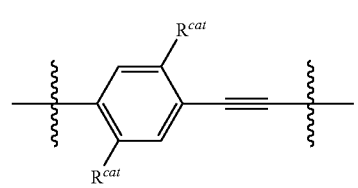

wherein $R^{cat}$ is as defined above, or,

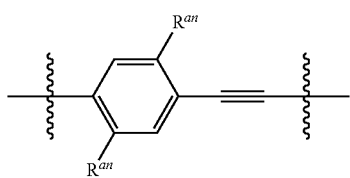

wherein $R^{an}$ is as defined above, or

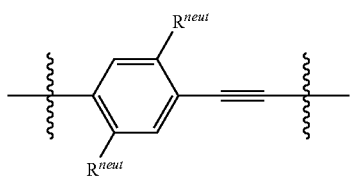

wherein $R^{neut}$ is an electrically neutral group, such as alkyl, alkoxy, or polyoxyalkylene, such as —O(CH$_2$CH$_2$O)$_p$CH$_2$CH$_2$OR wherein p=1, 2, 3, or more and R is alkyl, aryl, or the like. However, each oligomer must contain at least one cationic group.

For example, an oligomer can include alternating cationic and anionic substituted phenylethynyl repeating units, or alternating cationic and neutral phenylethynyl repeating unit, or can contain blocks of two or three of the repeating units types, provided that at least a single cationic group is present in the oligomer. Other arrangements will be apparent to the person of ordinary skill in the art. Such units can be interspersed with unsubstituted phenylethynyl or heteroarylethynyl groups in forming various embodiments of biocidal oligomers. The degree of polymerization can range from 2 up through several hundred, e.g., 2-500 arylethynyl or heteroarylethynyl repeating units, each of which can independently be unsubstituted or independently substituted with cationic, anionic, or neutral substituents.

For example, an oligomer that can be used in practicing a method of the invention can include, in addition to any of examples (A)-(E) shown above, any of the following exemplary oligomers:

(1)

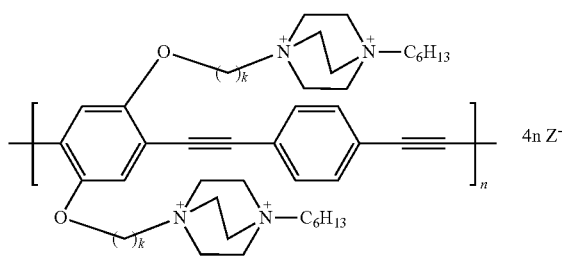

(2)

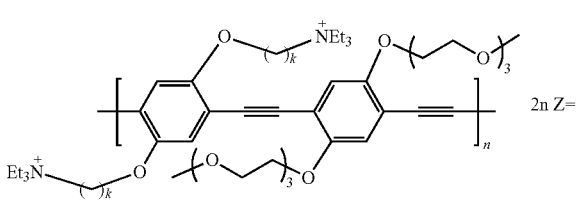

(3)

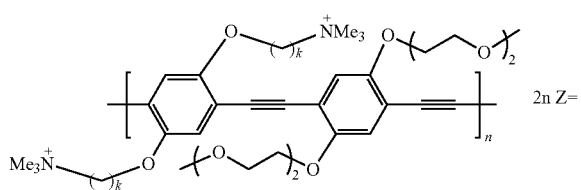

(4)

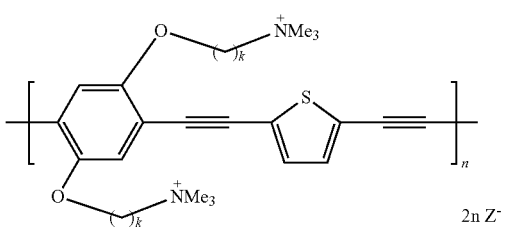

(5)

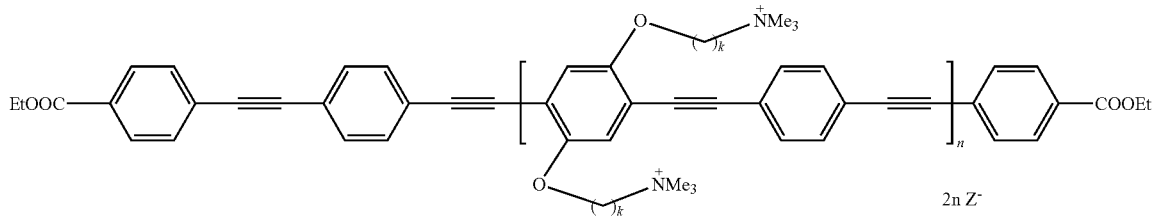

(6)

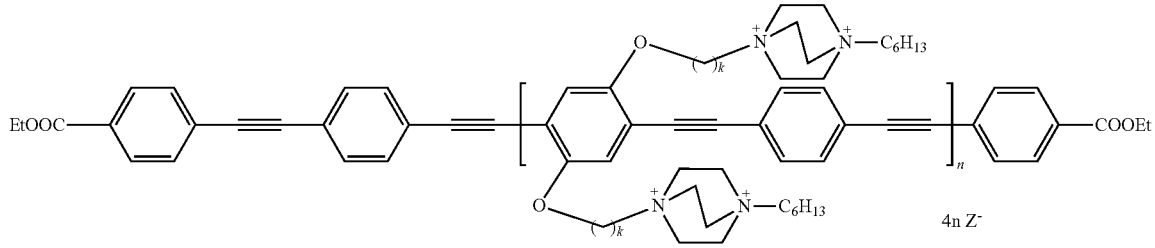

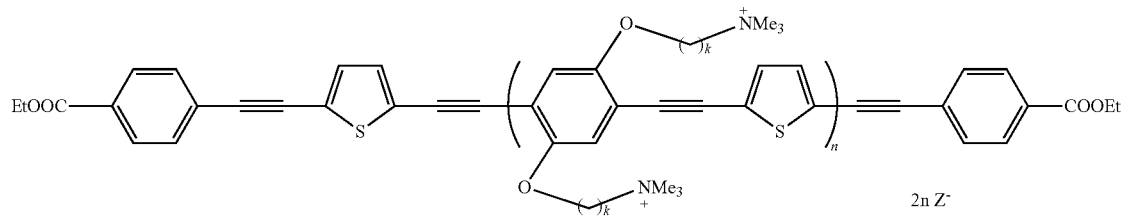

(7)

wherein for compounds 1-7, Z— is an anion, e.g. halide, sulfonate; k=1-6, n=1-100

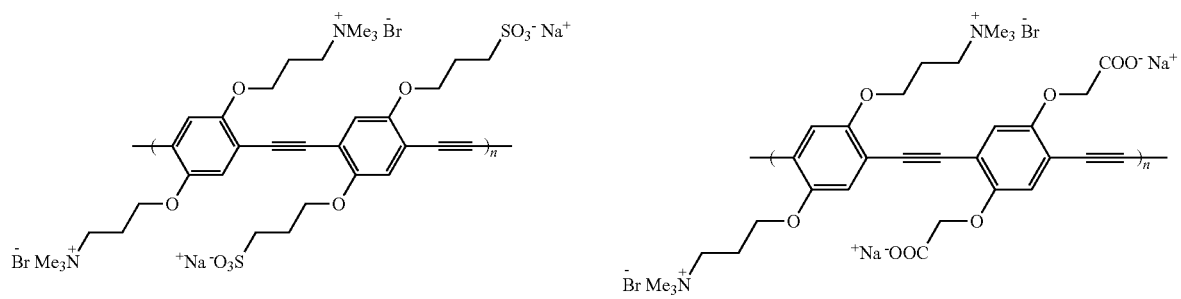

(8)

(9)

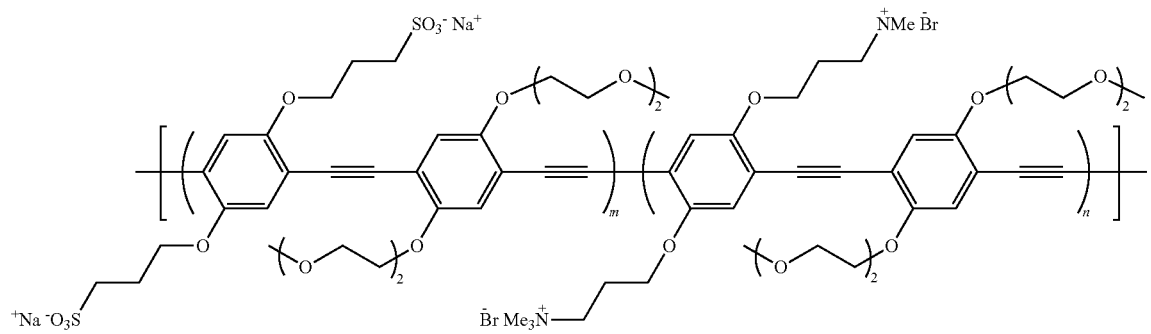

(10)

wherein for compound (10), m=1-10, n=1-10, degree of polymerization (DP)=1 to 100.

The DP of any of the compounds shown can be as defined above, in addition to the exemplary values shown with the figures; e.g., m or n can be 1 to about 500, or can be 1 to about 100, or can be 1 to about 50, or can be 1 to about 10. The terminal groups of the oligomers shown above can be any of the groups as defined for group X, above. Each k=1, 2, 3, 4, 5, or 6; the degree of polymerization n is 1 to 500, or is 1 to 100, or is 1 to 50, or is 1 to 10, and, for compounds 1, 2, 3, 4, 8, and 9, terminal groups of the oligomer are each an independently selected X as defined. The countions $Z^-$ can be any suitable anions. For any of the compounds (1)-(10), one or more additional X groups are optionally bonded at any available position(s).

The biocidal oligomer(s) selected for addition to the fiber-forming polymer prior to spinning, or selected for association with a preformed fiber, can be chosen for a particular use by the person of ordinary skill, based on the target or likely microorganism species to be controlled, and the relative toxicities of the various biocidal oligomers which can be prepared and tested as described herein.

In the various embodiments where the biocidal oligomer is added to a fiber-forming polymer prior to the step of spinning into the fiber, any spinnable polymer may be used. It is believed that the polymer can provide a structure to which the biocidal oligomer(s) selected for a particular use can associate non-covalently or, when provision is made for covalent bonding as is described in more detail below, for covalent attachment of the biocidal oligomer molecules to polymer molecules to provide the covalently modified polymer. Suitable polymers include, but are not limited to: both organic and inorganic polymers such as polycaprolactone (PCL), poly-alpha-hydroxyesters, e.g., poly-lactic-glycolic acid (PLGA), poly-lactic acid (PLA), poly-glycolic acid (PGA), other aliphatic polyesters such as glycol-type polyesters of dibasic aliphatic diacids, aromatic polyesters such as glycol-type polyesters of dibasic aromatic acids (terephthalate, etc.) polyvinyl alcohol (PVA), polyethylene oxide (PEO), or polyolefins such as polyethylene, polypropylene, polyethylene/polypropylene copolymers, polystyrene (PS), and the like; or the fiber-forming substances can be natural materials such as cellulose, chitosan, alginate, gelatin, and the like; or mixtures or blends thereof. Other fiber-forming polymers apparent to the person of ordinary skill can also be used, provided that a cationic oligo-(aryl/ heteroaryl-ethynyl) oligomer can be associated with the polymer or covalently bound thereto, or both.

According to an exemplary method of preparation of a biocidal fiber according to the present disclosure, a solution comprising the polymer and one or more biocidal oligomer can be delivered at a constant rate via a syringe pump; through a syringe fitted with stainless steel blunt tip needle. The needle is charged through a high voltage supply, and the resulting polymer fibers are collected on a grounded target to form a fibrous mat having antimicrobial properties.

As a specific example, a 3 wt % OPE/gram of polycaprolactone (PCL) in a 15 wt % dichloromethane (DCM) solution is stirred overnight at room temperature. Using a 2 ml plastic syringe (inner diameter (ID)=4.64 mm) equipped with an 18 gauge (g)×1.0 in. stainless steel blunt tip needle is used to deliver the PCL/DCM solution at a constant flow rate of 1.5 ml/hr and a voltage difference of 0.78 kv/cm (10 kv/13 cm) from tip to collector. It is notable that the voltage difference used for the OPE/PCL solution is different from that required to electrospin the PCL solution alone (0.83 kV/cm (i.e. 12.5 kv/15 cm)) due to the dielectric constant of the OPE/PCL solution compared to the PCL only solution.

Experiments were conducted to test the antimicrobial activity of the electrospun OPE/PCL mat. PCL only and OPE/PCL materials were exposed under both light and dark conditions to an *E. coli* culture and then stained with SYTOX Green, which stains only the dead bacteria. The stained bacteria were then observed with a FITC filter. FIGS. 6 and 7 show a control sample of *E. coli* alone. FIG. 6 is the bright field while FIG. 7 is the FITC filter. FIGS. 8 and 9 show the PCL only material after exposure to *E. coli* in dark conditions. No stained (i.e. dead) bacteria are seen. FIGS. 10 (bright field) and 11 (FITC) show the PCL-only material after exposure to *E. coli* in light conditions. (15 min. under 365 nm @ ~9 mW). It is believed that the few dead *E. coli* that are seen are due to the light exposure rather than any characteristic of the PCL-only material. FIGS. 12 (bright field) and 13 (FITC) show the OPE/PCL material after exposure to *E. coli* in dark conditions. The OPE used in the experiment is generally considered to be a light-activated biocide although, as shown, some activity under dark conditions is observed. FIGS. 14, 15 (bright field) and 16, 17 (FITC) show a very high degree of bacterial capture and kill.

It will be appreciated that careful selection of the carrier polymer and electrospinning conditions allow for the control and selection of various characteristics of the mat produced including, for example, the thickness, size, and composition. Furthermore, because it is possible to electrospin solutions containing particles, fillers, and other factors, a near infinite variety of antimicrobial mats have wide ranging properties can easily be produced. Examples of particles that could be incorporated into the electrospun mats include, but are not limited to: carbon nanotubes, titanium, silver, gold, and any other suitable nanomaterial. Furthermore, the carrier polymer can be selected based on properties such as degradation time, to produce a mat that releases the antimicrobial element (if a degradable carrier polymer is selected) or permanently secures the antimicrobial element (if a non-degradable carrier polymer is selected.)

Moreover, multi-layer mats could be produced with each layer having the same or different physical properties (i.e. thickness, porosity, etc.) and/or the same or different antimicrobial oligomers or polymers. The layers may be electrospun separately and then combined, or a subsequent layer or layers may be electrospun directly onto a first layer. For example, a multi-layered mat may be formed to incorporate layers formed from carrier polymers having different degradation times, effectively creating a mat having periodically time-released antimicrobial (or other) elements. Alternatively, or additionally, a manufacturer could produce a variety of single layers incorporating antimicrobial (or other) elements that are specific to one or more microbial agents (or other factors/conditions) and then quickly assemble "custom-made" mats in response to each customer's specific needs.

Potential uses for the mats described herein include, but are not limited to: filters, countertop coverings, tablecloths, curtains, swabs, bandages, wipes, tissues, coatings, liners, hospital garments, floor and wall coverings, medical devices, surgical instruments, gloves, masks, lab coats, gauze, orthopedic prostheses, bedding, mattress covers, dividers, linens, wound dressings, implants, and biological scaffolds. Their uses may be directed against known contamination, as in a wound infection, or applied as a deterrent to propagation of pathogenic agents in applications for common fomites.

Different blends to specifically release or retain killed bacteria could be developed based on combination of polymers with the desired retention properties. This could be effected either by use of varied polymer proportions in a single layer coating or by building multiple layers with the required external affinities.

In other embodiments, biocidal oligomers can be covalently bonded, either pre-spinning or post-spinning, to polymers that have been suitable functionalized. For example, a biocidal oligomer can be covalently bound to a suitably functionalized fiber-forming polymer by an acetylene-azide click reaction.

Accordingly, in various embodiments, one X group or other substituent of any one of formulas (F), (G), (H), or (J), or of any heteroaryl analog thereof; can comprise an ethynyl group. The fiber-forming polymer can comprise an azido group, such as by derivatization, and the biocidal oligomer and the polymer can be mutually covalently bonded using acetylene-azide click chemistry. Or, other click chemistry reactions known to the person of skill in the art can be used. By "click chemistry" is meant any of the highly efficient and versatile covalent bond forming reactions that can operate in the presence of a wide variety of functional groups. For example, see "Click Chemistry: Diverse Chemical Function from a Few Good Reactions," C. Kolb Hartmuth, M. G. Finn, K. Barry Sharpless, DOI: 10.1002/1521-3773 (20010601)40:11<2004: *Angewandle Chemie International Edition* (Jun. 1, 2001), 40(11), 2004-2021, incorporated by reference herein in its entirety.

The biocidal oligomer and the polymer can be covalently reacted using mutually reactive moieties disposed on the oligomer and the polymer, respectively. For example, the biocidal oligomer can comprises an electrophilic moiety and the polymer can comprise a moiety that can react with the electrophilic moiety to form a covalent bond. For example, the polymer can comprise an electrophilic acrylate group or a haloalkyl group or other alkylating moiety that is available to react with a nucleophilic substituent disposed on the biocidal oligomer, such as a hydroxyl group, an amino group, or the like.

Alternatively, the electrophile-nucleophile coupling can be oriented in the opposite configuration, wherein the biocidal oligomer comprises a nucleophilic moiety and the polymer contains a moiety that can react with the nucleophilic moiety to form a covalent bond. Examples of electrophile-nucleophile couplings to polymers are well known in the art, e.g., using nucleophilic groups such as hydroxyl, amino, and thio groups reactions with activated esters such as N-hydroxysuccinimide esters, haloacyl esters, and other electrophilic groups.

In various embodiments, the biocidal oligomer and the polymer can be mutually reacted prior to the step of spinning, to provide a spun fiber comprising a covalent conjugate comprising a biocidal oligomer component and a fiber-forming polymer component, wherein the spun fiber possesses biocidal properties versus microorganisms in the presence of oxygen. Or, the reactive precursor materials of the fiber-forming polymer and the biocidal oligomer can be mixed and spun, such that reaction occurs under conditions of spinning (e.g., with heating, drying, and the like). Alternatively, the polymer can be spun into a fiber, which can then be treated with a biocidal oligomer that adheres to the fiber non-covalently or reacts with the polymer of the fiber covalently, or a combination.

As described above, in various embodiments the biocidal properties of the spun fiber versus microorganisms in the presence of oxygen is increased under illumination by visible or ultraviolet light. It is believed by the inventors that the biocidal oligomers can catalyze the formation of singlet oxygen from molecular oxygen present in the environment, and this generation of the toxic and reactive singlet oxygen, which can be the effective toxic agent acting to kill the microorganisms, is enhanced in the presence of activating photons of actinic radiations such as visible light and/or ultraviolet (UV) light. The absorptivity, e.g., the extinction coefficient, of the biocidal oligomer chosen for use in the fiber or fiber nonwoven mat to render them antimicrobial, can be selected based upon the intended wavelength of illumination to be used; for example, a fiber or product made therefrom adapted to be biocidal under visible illumination, such as daylight or artificial interior lighting, can be formed comprising a biocidal oligomer structure that is a potent absorber of light of those wavelengths. It is believed that singlet oxygen generation rates are correlated with photo absorption efficiencies under comparable conditions of exposure and oxygen content in the environment. It is believed that the oligomers herein are activated by absorption of a photon into an electronically excited state, which excitation energy is transferred to molecular oxygen present in the vicinity.

See also: L. Ista, et al., dx.doi.org/10.1021/la105018g|Langmuir 2011, 27, 4956-4962; E. Ji. et al. dx.doi.org/10.1021/la2018192|Langmuir 2011, 27, 10763-10769; E. Ji, et al., dx.doi.org/10.1021/am200644g|ACS Appl. Mater. Interfaces 2011, 3, 2820-2829; S. Chemburu, et al., Langmuir 2008, 24, 11053-11062; the disclosures of which are incorporated herein by reference in their entireties.

Click Chemistry: Formation of Covalent Conjugates of Biocidal Oligomers

The present disclosure provides a novel method to covalently attach antimicrobial end-only functionalized oligo (phenylene ethynylene) (EO-OPEs) onto the surfaces of silica beads using "click chemistry". Examples of "click chemistry" reactions are described, for example, in Huisgen, R. *Proceedings of the Chemical Society of London* 1961, 357, and Cedric, H.; Christophe, C. *Journal of Organic Chemistry* 2003, 68, 2167, both of which are hereby incorporated by reference. The Cu(I)-catalyzed 1,3-dipolar azide-alkyne cycloaddition (CuAAC) (i.e., the acetylene-azide click reaction) is a powerful tool for immobilization of functional groups on silica beads, polymers beads and cotton.

The present invention can provide a novel method to covalently attach antimicrobial end-only functionalized oligo(phenylene ethynylene) (EO-OPEs) onto appropriately treated or derivatized solid substances, such as fiber-forming polymers, or onto other solid materials that can be used for antimicrobial action, such as silica gel. The covalent bonding can be carried out using "click chemistry" type reactions, as described above.

For example, to demonstrate the effectiveness of using click chemistry to bond biocidal oligomers to solids, such as particles or fibers, surface modification of 300 nm diameter silica particles was accomplished by the reaction of the silica surface with trimethoxysilane bearing a chloride group, which was then substituted by reaction with sodium azide to obtain azide-functionalized silica surface, according to the following Scheme S3.

Scheme S3: Azide-ethynyl click chemistry coupling reaction of oligomer with silica particles

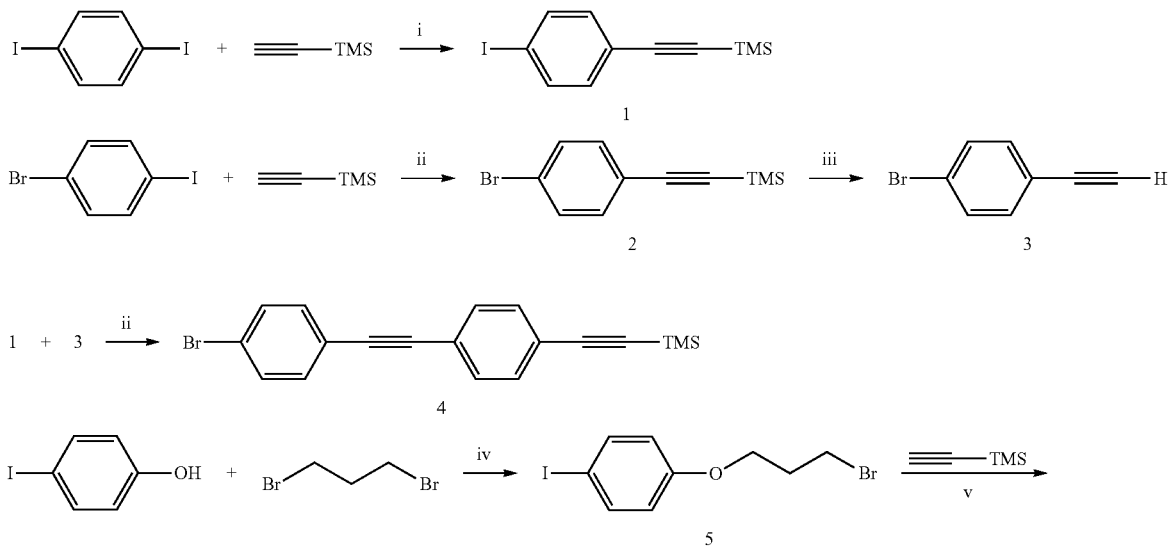

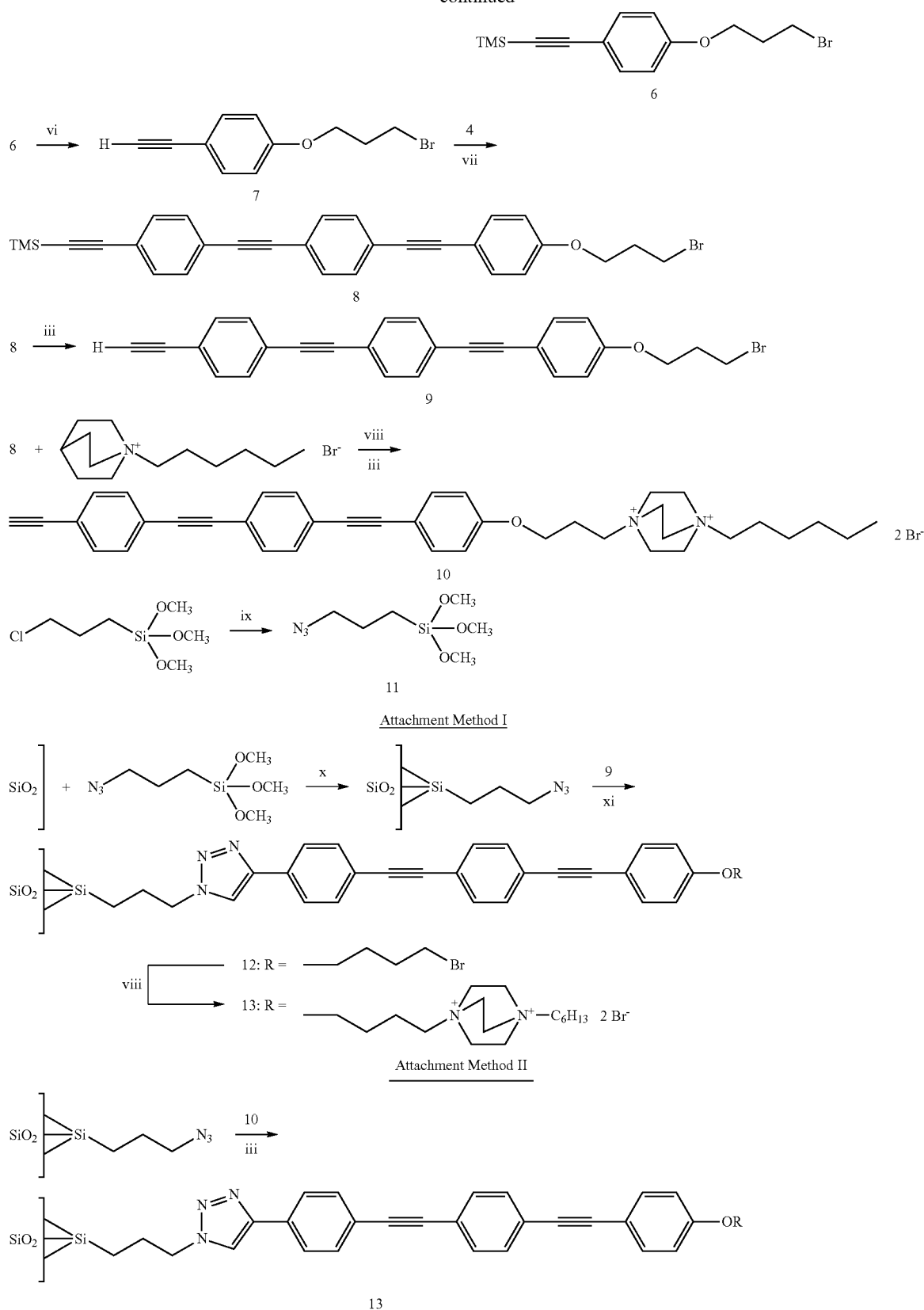
(i) Pd(PPh₃)₂Cl₂, CuI, THF/Et₃N, 40° C. (ii) Pd(PPh₃)₂Cl₂, CuI, (iPr)₂NH, 50° C. (iii) TBAF, CH₂Cl₂. (iv) NaOH, H2O. (v) Pd(PPh₃)₂Cl₂, CuI, Et₂N. (vi) K₂CO₃, CH₃OH (vii) Pd(PPh₃)₂Cl₂, CuI, THF/(iPr)₂NH, 70 ° C. (viii) DMA, reflux. (ix) NaN₃, DMF. (x) toluene, 70-75° C. (xi) CuSO4, ascorbate, CHCl₃/DMF A biocidal oligomer bearing a terminal ethynyl moiety (OPEC1) was coupled to an azide-functionalized surface, e.g. an azide-functionalized silica particle surface using click chemistry, followed by alkylation of tertiary amines to introduce the cationic quaternary ammonium group.

The surface modification process was monitored by infrared spectroscopy (FTIR) and thermogravimetric analysis (TGA). As shown in FIG. 18, the unmodified silica particles (SiO$_2$—OH) exhibited a strong peak at 1110 cm$^{-1}$ which was assigned to the Si—O—Si asymmetric stretch. In addition, a broad peak centered at 3400 cm$^{-1}$ was due to OH stretch from both the silanol and adsorbed water. The FTIR spectrum of SiO$_2$-Azide gave clear evidence for the presence of the azide groups. The peak at 2100 cm$^{-1}$ corresponded to the stretch of the azide group. In addition, multiple weak peaks around 2900 cm$^{-1}$ indicated the presence of sp$^3$ C—H bonds. After the Click reaction, the peak at 2100 cm$^{-1}$ disappeared completely, confirming the success of the Click reaction with all the azide units reacted. In addition, the peaks around 1600 cm$^{-1}$ confirmed the presence of aromatic compounds on the silica particles (SiO$_2$-OPEC1).

To monitor the surface modification process, thermogravimetric analysis (TGA) was used. FIG. 19 shows the TGA analysis of unmodified silica particles (SiO$_2$—OH), azide-modified silica particles (SiO$_2$—N$_3$) and OPEC1-grafted silica particles (SiO$_2$-OPEC1). The loss bellow 200° C., due to the physisorbed water and residual organic solvent, was 6.8% for unmodified silica particles (FIG. 19A). At 700° C., we observed a weight loss of 3% (FIG. 19B) for the azide-modified silica particles in the TGA curve, which was attributed to the presence of spacer trimethoxysilylpropyl azide. The residual mass percentage was 88% and the surface grafting density of azide groups was calculated to be about 9.3 chains/nm$^2$ to the eq 1. FIG. 19C shows the TGA curve of the OPEC1-grafted silica particles. It shows that the weight loss percentage corresponding to the decomposition of OPEC1 chains was 8%, and the residue mass percent was 80% at 700° C. The surface grafting density of OPEC1 was found to be about 8.3 chains/nm$^2$ calculated from eq 1, below, according to the TGA analysis.

$$\delta = \frac{\left(\frac{W_{Org}}{W_{inorg}}\right)W_{SiO2}N_A}{M_{Org}SA} \qquad \text{Eq. (1)}$$

Here, $W_{Org}$ is the weight loss percentage corresponding to the decomposition of the organic component, $W_{Inorg}$ is the residual weight percentage, $W_{SiO2}$ is the weight of silica particles (3.69E−14 g/sphere), $N_A$ is Avogadro's number, $M_{Org}$ is the molecular weight of the organic component, and SA is the surface area of silica particles (3.42E+05 nm$^2$).

Transmission electron microscopy (TEM) was used to determine the morphology and texture of the silica particle surfaces. As shown in FIGS. 20A-C, unmodified silica particles (FIG. 20A) had clean, smooth and spherical surfaces and the azide-modified silica particles (FIG. 20B) appeared about the same. This can be explained by the small amount of organic material on the silica particle surfaces. However, the OPEC1 grafted silica particles (FIG. 20C) showed a rough irregular surface, corresponding to the presence of organic material. The organic compounds formed a layer outside the surface of silica particles and thus changed the shapes of the particles.

Scanning electron microscopy images provide information about the surface shapes and features. As shown in FIGS. 21A and 21B, respectively, the unmodified and azide-modified silica particles had smooth uniform surfaces. In contrast, the SEM image of OPEC1-grafted silica particles (FIG. 21C) clearly showed the organic layer outside the surface. However, the covering was not very uniform. Most of the surfaces were covered by organic material, but at some places, there were some large aggregates, which may be multiple layers. Another possibility is that some organic material was chemically or physically adsorbed on the surfaces.

The fluorescence spectra of OPEC1-grafted silica particles and unmodified silica particles in methanol are shown in FIGS. 22 and 23, respectively. The unmodified silica particles did not show any fluorescence. The peaks at about 350 nm were due to light scattering since the silica particles are around 300 nm in diameter. The fluorescence profile of OPEC1-grafted silica particles was similar to the pure OPEC1 in methanol solution. Compared to the fluorescence OPEC1 in methanol solution, the fluorescence spectrum of OPEC1 grafted silica particles was broader and weaker, because of the aggregates of the oligomers on the surfaces.

It has been shown that singlet oxygen is the active species that can kill the bacteria in the biocidal process. Singlet oxygen spectrum of OPEC1-grafted silica particles was measured in d-methanol. After purging oxygen for one-half hour, the OPEC1-grafted silica particles were excited at 320 nm, and the emission signal of singlet oxygen at 1270 nm appeared (FIG. 24). This spectrum strongly supported the application of OPEC1-grafted silica particles as an antibacterial material. However, the signal was rather weak compared to the singlet oxygen spectra of oligo(phenylene ethynylene) and poly(phenylene ethynylene) solutions. One possibility is that the concentration of the OPEC1 in the silica particle suspension is much lower. In addition, the formation of aggregates on the surface of silica particles may impair the ability to generate singlet oxygen.

Recently we have synthesized OPE-DABCO and EO-OPE DABCO

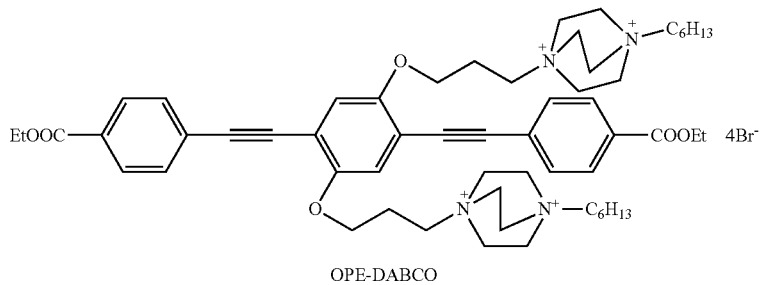

OPE-DABCO

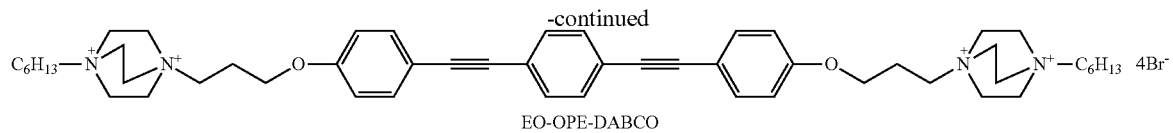
EO-OPE-DABCO containing quaternary ammonium pendant groups based on 1,4-diazabocyclo-[2.2.2.]-octane (DABCO). It has been shown that the incorporation of the DABCO group into antimicrobials might amplify its ability to diffuse into the bacterial cell wall due to similarities between this moiety and the lipid layer. [Ref: Kenawy, E. R., S. D. Worley, and R. Broughton. *The chemistry and applications of antimicrobial polymers: A state-of-the-art review*. Biomacromolecules, 2007. 8(5): p. 1359-1384] Therefore, the binding of antimicrobials to the cytoplasmic membrane of the bacteria is increased by both ionic and van der Waals interactions. [Ref:Kenawy, E. R., S. D. Worley, and R. Broughton. *The chemistry and applications of antimicrobial polymers: A state-of-the-art review*. Biomacromolecules, 2007. 8(5): p. 1359-1384] These two oligomers have been employed to compare their antimicrobial activity both in the dark and under the UV light in regard to their structure difference. After 10 min of UV irradiation of two oligomers, EO-OPE-DABCO (1 µg/mL) shows 100% killing against *S. aureus* while OPE-DABCO deactivates ~75% bacteria and its antibacterial efficiency increases with increasing irradiation time up to ~99% deactivation (FIG. 25). EO-OPE-DABCO also shows significant dark killing: fewer than 10% of the bacteria survive after incubation with EO-OPE-DABCO for 10 min in the dark.

EO-OPE-DABCO has been covalently attached to alkylazide functionalized glass surface via Cu-catalyzed click chemistry. [*Chem. Mater.*, 2010, 22 (18), pp 5319-5327 and *Langmuir*, 2011, 27 (1), pp 328-334]

See also: K. Ogawa, et al., *Langmuir* 2007, 23, 4541-4548; the disclosure of which is incorporated herein by reference in its entirety.

EXAMPLES

Materials

All chemicals used for synthesis were of reagent grade and used without further purification. Details of the synthesis and characterization of oligomer (A)-(C) are described in the supporting information. Compound (D) and (E) were synthesized according to previously described procedures.[16] The photophysical characterization of all compounds is also described in the supporting information.

Synthetic Procedures

Compound 6

1-Hexyl-4-aza-1-azoniabicyclo[2.2.2]octane Bromide (2) and 1,4-bis(3-bromopropoxy)-2,5-diiodobenzene (5) were prepared according to a literature procedure. (See: Zhao, X. Y.; Pinto, M. R.; Hardison, L. M.; Mwaura, J.; Muller, J.; Jiang, H.; Witker, D.; Kleiman, V. D.; Reynolds, J. R.; Schanze, K. S. Variable band gap poly(arylene ethynylene) conjugated polyelectrolytes, *Macromolecules* 2006, 39, 6355; McQuade, D. T.; Hegedus, A. H.; Swager, T. M. Signal amplification of a "turn-on" sensor: Harvesting the light captured by a conjugated polymer, *Journal of the American Chemical Society* 2000, 122, 12389). A solution of 0.35 g (1.25 mmol) of compound 1 and 0.3 g (0.5 mmol) of compound 5 in 5 mL of dimethyacetamide was stirred at 110° C. overnight. Upon cooling, 10 mL of cold ether was added to the reaction mixture. The resulting precipitates was collected by filtration and purified by hot filtration. White powder was recrystallized from water, yield 0.3 g (0.26 mmol, 52%). $^1$H NMR (500 MHz, DMSO-d6) δ 3.24 (s, 1H), 3.24 (s, 1H), 3.89-4.08 (br, 32H), 3.72 (br, 4H), 3.54 (br, 4H), 2.23 (br, 4H), 1.69 (br, 4H), 1.31 (br, 12H), 0.88 (br, 6H).

Compound 9

1.33 g (14 mmol) oftrimethylsilylacetylene was added to a deoxygenated solution of 2.56 g (9.1 mmol) of compound 7, 102 mg (0.15 mmol) of Pd(PPh$_3$)$_2$Cl$_2$, and 42 mg (0.22 mmol) of CuI in 30 mL of Et$_3$N. The reaction solution was stirred at room temperature under argon overnight. The solvent was removed, and the solid was purified by flash chromatography on silica gel with hexane to yield a compound 8 (1.81 g, 81%). A solution of 0.81 g (3.29 mmol) of compound 8 in 20 mL of methanol was deoxygenated for 30 min and 1.0 M tetrabutylammonium fluoride solution in THF (9.95 mmol) was added to the flask under argon and the mixture was stirred at room temperature for 6 h. The solvent was removed and re-dissolved in methylene chloride and extracted with water twice. The combined organic solution was dried over MgSO$_4$ and the solvent was removed at reduced pressure to yield a compound 9 (0.38 g, 66%). $^1$H NMR (500 MHz, CDCl$_3$) δ 7.80 (d, 2H), 7.54 (d, 2H), 4.38 (m, 2H), 3.24 (s, 1H), 1.39 (t, 3H).

OPE-1-DABCO (Oligomer (A))

A solution of 0.1 g (0.087 mmol) of compound 6 and 0.033 g (0.191 mmol) of compound 9 in 4 mL of DMF/(iPr)$_2$NH mixture was deoxygenated for 30 min. 4 mg (3 µmol) of Pd(PPh$_3$)$_4$, and 1 mg (5 µmol) of CuI were added and the resulting mixture was stirred at room temperature under argon for 18 h. The reaction solution was poured into 100 mL of acetone. The precipitated solid was collected by vacuum filtration and recrystallized from water, yield 0.09 g (85%). $^1$H NMR (500 MHz, DMSO-d6) δ 8.04 (br, 4H), 7.71 (br, 4H), 7.36 (br, 2H), 4.33 (br, 4H), 4.19 (br, 4H), 3.95-3.74 (br, 28H), 3.51 (br, 4H), 2.07 (br, 4H), 1.68 (br, 4H), 1.31 (br, 18H), 0.89 (br, 6H). $^{13}$C NMR (500 MHz, DMSO-d6) δ 165.11, 152.93, 131.71, 129.72, 129.57, 126.83, 117.56, 113.30, 94.37, 88.56, 66.26, 63.38, 50.57, 50.41, 30.59, 25.16, 21.96, 21.80, 21.27, 14.16, 13.91. ESI MS calcd m/z for [M+2Br]$^{2+}$ 545.2289. found 545.2295.

Compound 14a 1-(3-bromopropoxy)-4-iodo benzene (12) and 1,4-diethynyl benzene (13a), and were prepared according to a literature procedure. (See: Zhao, X. Y.; Pinto, M. R.; Hardison, L. M.; Mwaura, J.; Muller, J.; Jiang, H.; Witker, D.; Kleiman, V. D.; Reynolds, J. R.; Schanze, K. S. Variable band gap poly(arylene ethynylene) conjugated polyelectrolytes. *Macromolecules* 2006, 39, 6355; Capuano, B.; Crosby, I. T.; McRobb, F. M.; Podloucka, A.; Taylor, D. A.; Vom, A.; Yuriev, E. The Synthesis and Preliminary Pharmacological Evaluation of a Series of Substituted 4'-Phenoxypropyl Analogues of the Atypical Antipsychotic Clozapine, *Australian Journal of chemistry* 2010, 63, 116). 61 mg (53 µmol) of Pd(PPh$_3$)$_4$ and 10 mg (53 µmol) of CuI were added to a deoxygenated solution of 1.00 g (2.93 mmol) of compound 12 and 0.17 g (1.33 mmol) of compound 13a in 20 mL of $CHCl_3/(iPr)_2NH$ (v/v=1/1) and stirred at room temperature under argon for 2 days. The solvent was removed and the solid was purified by flash chromatography on silica gel with chloroform to yield a compound 14a (0.60 g, 82%). $^1H$ NMR (500 MHz, $CDCl_3$) δ 7.47 (d, 2H), 6.89 (d, 2H), 4.13 (t, 4H), 3.62 (t, 4H), 2.34 (m, 4H). $^{13}C$ NMR (500 MHz, $CDCl_3$) δ 158.84, 133.12, 131.33, 123.07, 114.59, 102.96, 91.08, 88.04, 65.37, 32.26, 29.82.

EO-OPE-DABCO (Oligomer (B))

A solution of 0.77 g (2.79 mmol) of compound 2 in 6 mL of DMA was added to a solution of 0.56 g (1.02 mml) of compound 14a in 30 mL of DMA and the mixture solution was stirred at 110° C. for 1 day. The reaction solution was poured into 300 mL of acetone. The resulting precipitates was collected by filtration and washed with acetone and chloroform. After drying 1.04 g (0.94 mmol, 92%) was obtained. $^1H$ NMR (500 MHz, DMSO-d6) δ 7.53 (d, 8H), 7.02 (d, 4H), 4.13 (br, 4H), 3.96-3.86 (br, 24H), 3.71 (br, 4H), 3.51 (br, 4H), 2.23 (br, 4H), 1.69 (br, 4H), 1.31 (br, 12H), 0.88 (br, 6H). $^{13}C$ NMR (500 MHz, DMSO-d6) δ 158.57, 138.04, 133.11, 131.46, 122.46, 117.40, 115.07, 114.39, 91.39, 87.84, 64.67, 63.38, 61.06, 50.56, 50.40, 30.59, 25.18, 21.81, 21.28, 13.82. ESI MS calcd m/z for $[M+2Br]^{2+}$ 473.2077. found 473.2092.

Compound 14b 2,5-Bis((trimethylsilyl)ethynyl)thiophene (13b) was prepared according to a literature procedure. (See: Corbitt, T. S.; Ding, L. P.; Ji, E. Y.; Ista, L. K.; Ogawa, K.; Lopez, G. P.; Schanze, K. S.; Whitten, D. G. Light and dark biocidal activity of cationic poly(arylene ethynylene) conjugated polyelectrolytes. *Photochemical & Photobiological Sciences* 2009, 8, 998). 0.14 g (0.52 mmol) of compound 13b in 20 mL of $CHCl_3/(iPr)_2NH$ (v/v=1/1) was deoxygenated for 15 min and followed by the addition of TBAF (5.2 mmol). The solution was stirred at room temperature under argon for 30 min. 0.36 g (1.04 mmol) of compound 12, and 35 mg (50 µmol) of $Pd(PPh_3)_2Cl_2$ and 10 mg (53 µmol) of CuI were added to the resulting solution and stirred at stirred at room temperature under argon for 3 days. The solvent was removed and the solid was purified by flash chromatography on silica gel with chloroform to yield a compound 14b (0.09 g, 31%). $^1H$ NMR (500 MHz, $CDCl_3$) δ7.45 (d, 2H), 7.11 (s, 1H), 6.82 (m, 4H), 4.14 (t, 4H), 3.75 (t, 4H), 2.25 (m, 4H). $^{13}C$ NMR (500 MHz, $CDCl_3$) δ 159.05, 134.08, 133.05, 131.38, 124.60, 114.96, 114.61, 93.91, 81.20, 64.35, 41.38, 32.16.

EO-OPE1-Th-DABCO (Oligomer (C))

This oligomer was synthesized in the same procedure described for EO-OPE-DABCO using compound 14b (46 mg, 0.08 mmol) and compound 2 (62 mg, 0.22 mmol). Yield: 30 mg, 37%. Due to the limited solubility of this oligomer, only partial aromatic carbon $^{13}C$ NMR peaks and m/z for $[M-C_6H_{13}+Br]^{2+}$ have been observed. $^1H$ NMR (500 MHz, DMSO-d6) δ 7.52 (m, 4H), 7.34 (s, 2H), 7.01 (d, 4H), 4.13 (br, 4H), 3.91-3.87 (br, 24H), 3.71 (br, 4H), 3.33 (br, 4H), 2.19 (br, 4H), 1.68 (br, 4H), 1.30 (br, 12H), 0.88 (br, 6H). $^{13}C$ NMR (500 MHz, DMSO-d6) δ 159.79, 134.13, 133.09, 132.60, 115.18, 115.11, 115.04, 79.20, 64.68, 64.58, 63.38, 50.55, 50.39, 31.55, 30.58, 25.17, 21.79, 21.24, 13.81. ESI MS calcd m/z for $[M-C_6H_{13}+Br]^{2+}$ 394.1774. found 394.1760.

Photophysical Characterization

Figure 1A:
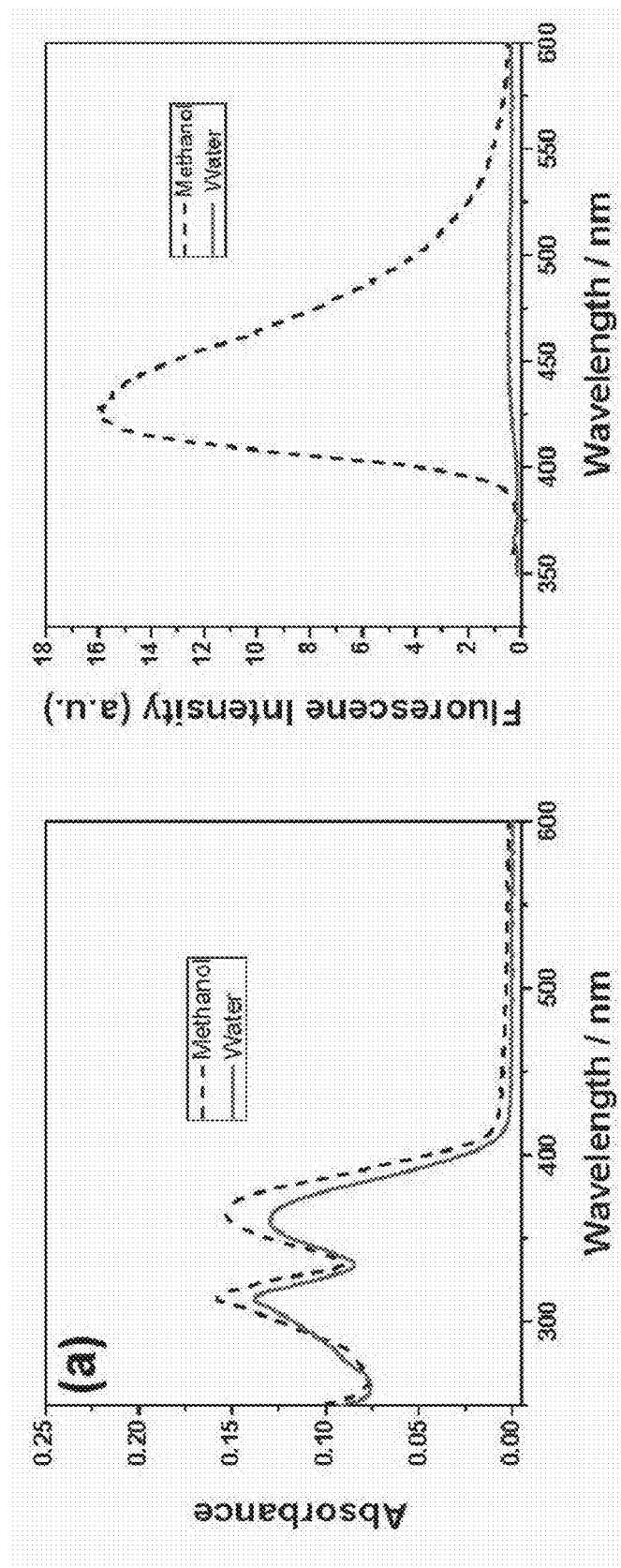
FIG. 1 shows absorption (left) and fluorescence spectra (right) of oligomers, (1A) oligomer (A) and, (1B) oligomer (B) in methanol and water.
Figure 1B:
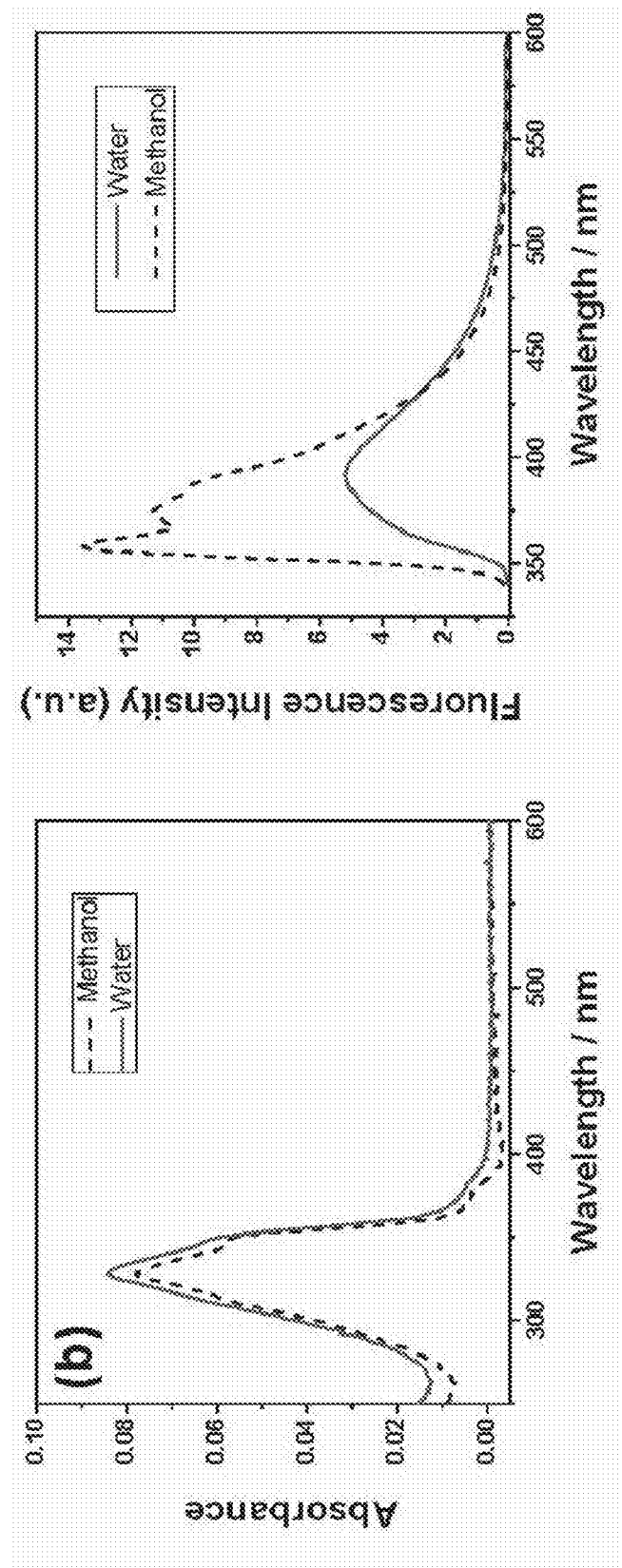
Figure 2A:
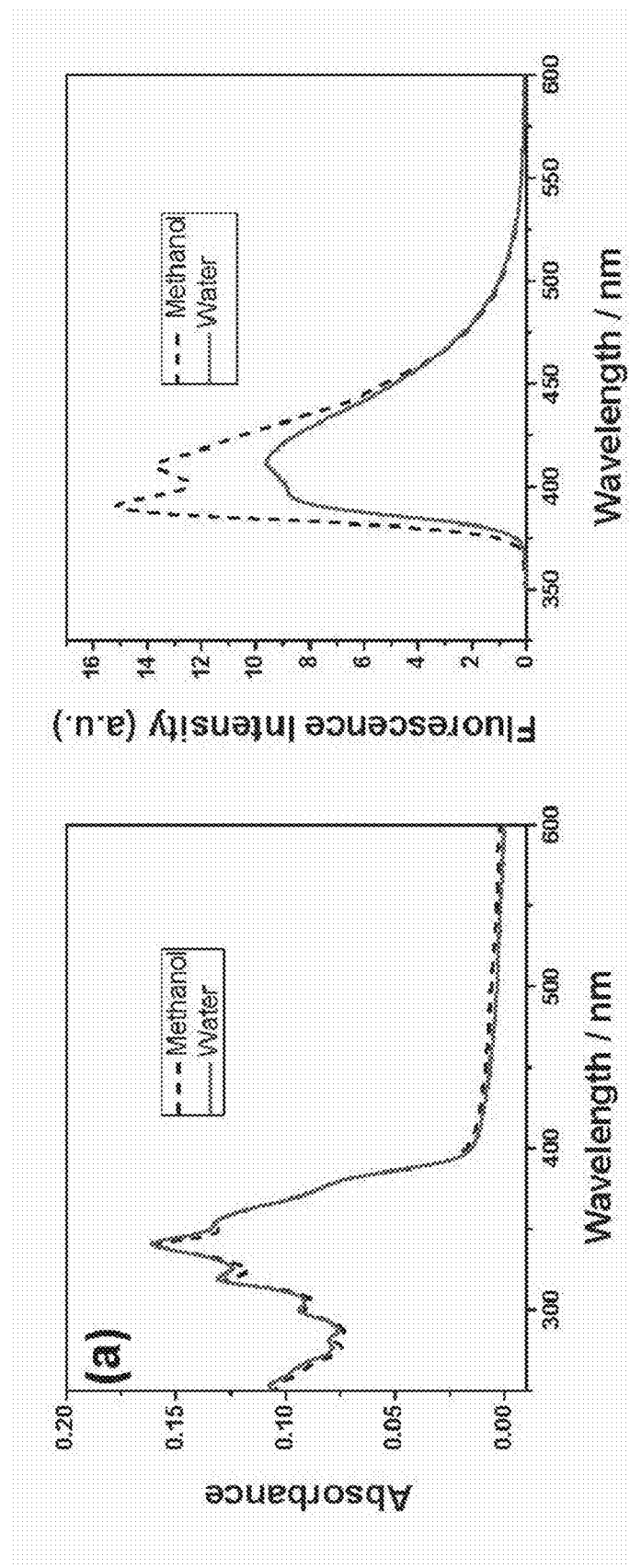
FIG. 2 shows absorption (left) and fluorescence spectra (right) of oligomers, (2A) oligomer (C) and, (2B) oligomer (D) in methanol and water.
Figure 2B:
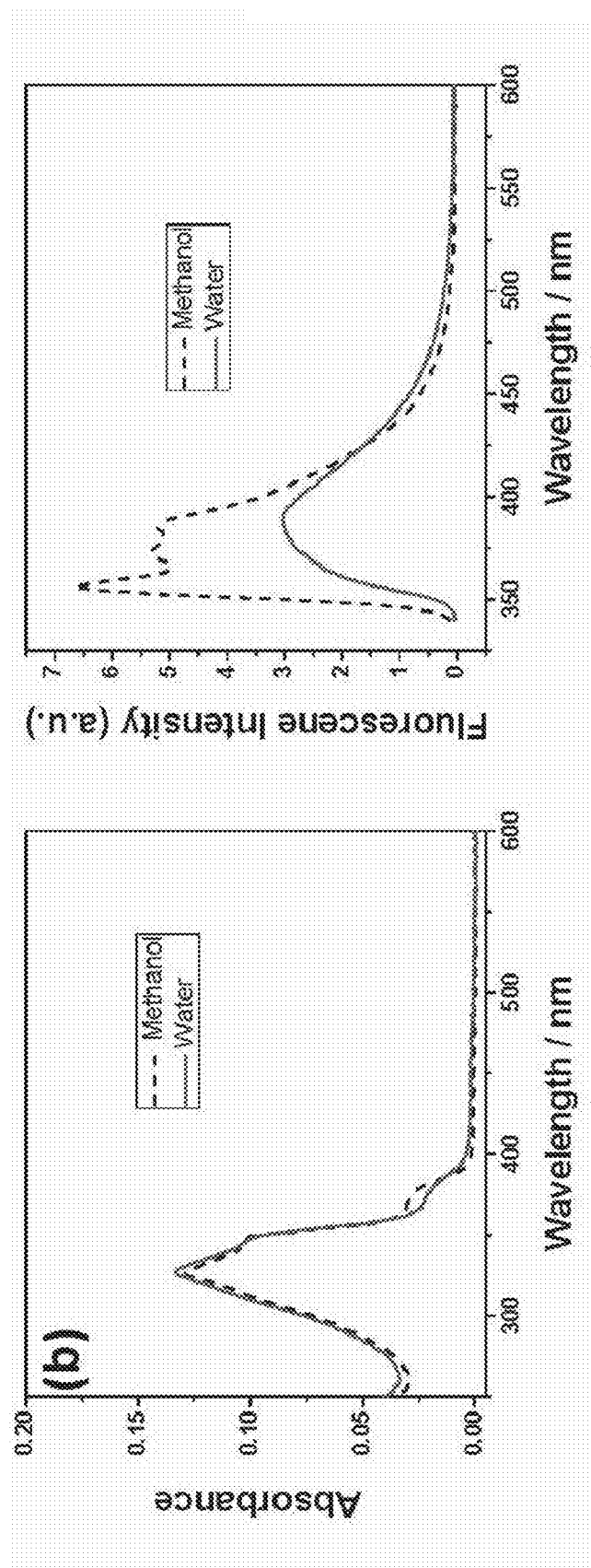
Figure 3A:
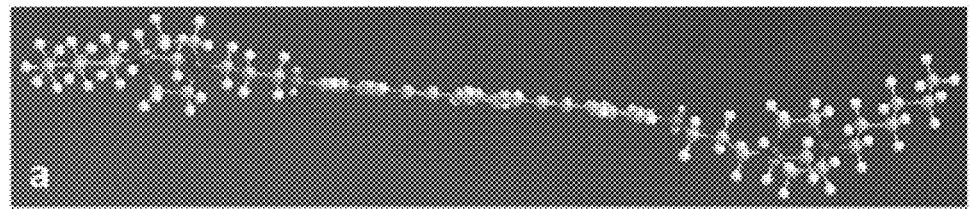
FIG. 3 shows absorption (left) and fluorescence spectra (right) of oligomer (E) in methanol and water.
Figure 3B:
Figure 3C:
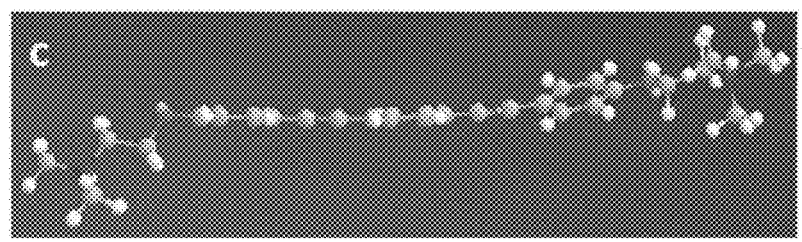
Figure 3D:

Absorption and fluorescence spectra were recorded on a Cary 100 UV-Vis spectrophotometer and a Photon Technology International spectrofluorometer, respectively. The optical density of the solutions was adjusted to ~0.7 at the excitation wavelength (355 nm) with the laser energy set at ~7 mJ. Solutions were purged with argon for 45 min before making transient absorption spectroscopy measurements. Singlet oxygen quantum yields were measured using a Photon Technology International Quantamaster near-IR spectrophotometer equipped with an InGaAs photodiode detector, optical chopper and a lock in amplifier. See Table 1 and FIGS. 1-3 for results.

Transient absorption difference spectra of oligomers were determined for oligomer (A) (initial delay=70 ns, subsequent delay increment=2 µs) and for oligomer (B) in methanol (initial delay=70 ns, subsequent delay increment=2 µs) (OD ~0.7 at 355 nm and excited with the laser energy of ~7 mJ in each case), and each showed a steady decrease in the transient difference in optical density. For oligomer (A) the transient difference spectrum was a monotonic curve with a maximum at about 580 nm, and for (B) the transient difference spectrum was a substantially monotonic curve with a maximum at about 560 nm but with a shoulder at about 610 nm.

Transient absorption difference spectra of oligomers were determined for oligomer (C) (initial delay=70 ns, subsequent delay increment=1 µs), and for oligomer (D) in methanol (initial delay=70 ns, subsequent delay increment=1 µs) (OD ~0.7 at 355 nm and excited with the laser energy of ~7 mJ in each case), and each showed a steady decrease in the transient difference in optical density. For oligomer (C) the transient difference spectrum was a monotonic curve with a maximum at about 500 nm, and for (D) the transient difference spectrum was a substantially monotonic curve with a maximum at about 610 nm but with a shoulder at about 590 nm.

Transient absorption difference spectra of oligomer (E) was determined (initial delay=70 ns, subsequent delay increment=2 µs) in methanol (initial delay=70 ns, subsequent delay increment=2 µs) (OD 0.7 at 355 nm and excited with the laser energy of ~7 mJ), and showed a steady decrease in the transient difference in optical density. The transient difference spectrum was a substantially monotonic curve with a maximum at about 520 nm.

Biofilm Growth in the Calgary Biofilm Device

*Escherichia coli* K-12 was obtained from the American Type Culture Collection (ATCC #10798), revived in Luria Broth (LB, Sigma) and stored in LB with 20% (v/v) glycerol at −70° C. Stock cultures maintained on agar (2% Difco) plates of LB were used to inoculate 50 mL cultures in liquid LB. *E. coli* was grown at 37° C. for 18 h. Bacteria were grown as a microbial biofilm using a Calgary Biofilm Device (CBD), commercially available as the MBEC™ assay, featuring 96 pegs protruding down from a microtiter plate lid and fitting into the wells of a standard 96-well microtiter plate. This device allows 96 identical biofilms to grow on the pegs at a time. Biofilms of *E. coli* were grown in each well using 150 µL of the culture diluted to $1\times10^7$ CFU (colony forming unit) following previous calibration. The biofilms were grown at 37° C. for 24 h in a shaker at 150 rpm.

Determination of the Minimum Inhibitory Concentration

The minimum inhibitory concentration (MIC) represents the lowest concentration of antimicrobial required to inhibit the visible growth of a planktonic bacterial population. The MIC was determined using the CBD.[17, 18, 20] Biofilms were formed on the peg surface of the CBD as described above and then transferred to a 96-well microtiter plate containing 200 µL of saline (0.85% NaCl aqueous solution) and washed for 5 min to remove non-adherent bacteria. The biofilms were transferred to a plate containing 200 µL of LB with a gradient concentration of the OPEs (challenge plate). Each concentration was repeated eight times (one row of the plate). The biofilms were then incubated in the dark at 37° C. for 24 h. To determine the MIC, the growth of bacteria was evaluated in the challenge plate after incubation. The optical density of each well was measured at 600 nm and the MIC was calculated for 90% inhibition of growth compared with biofilms grown in LB only.

Determination of Minimum Biofilm Eradication Concentration.

The Minimum biofilm eradication concentration (MBEC) is the lowest concentration at which bacteria from a biofilm fail to regrow. The MBEC was also measured using the CBD and detailed procedure has been described elsewhere.[17, 18, 20] Biofilms were formed and washed as described above. The biofilms were then transferred to a plate containing saline with a gradient concentration of the OPEs (challenge plate). The samples exposed to light were incubated for 1 h in a LuzChem ORG photoreactor using Hitachi FL8BL-B ($\lambda$=300-400 nm) lamps, whereas the samples kept in the dark, were incubated for 24 h in a shaker at 150 rpm. The biofilms were then removed from the challenge plate and washed twice in a plate of saline solution to remove traces of OPEs. The biofilms were placed in a plate containing LB media (recovery plate) and sonicated for 10 min in an ultrasonic cleaner (VWR 97043-964) in order to recover the biofilm in the media solution through vibration. The recovery plate containing the biofilms was incubated in the dark at 37° C. for 24 h. To determine the MBEC, the growth of bacteria was evaluated in the recovery plate after incubation. The optical density of each plate was measured at 600 nm and the MBEC obtained for the concentration that showed clear wells. Bacterial grown in a specific well indicates regrowth of planktonic bacteria from surviving biofilm, while clear wells indicate the eradication of the biofilms and the lack of bacteria regrowth.

Efficacy of EO-OPEs in Killing Biofilm Bacteria.

Biofilms of E. coli were uniformly formed on the CBD surface after 24 h of incubation (FIG. 8) and examined to determine the biocidal activity of OPEs. To that end, both the MIC and MBEC of each oligomer (A)-(E) were measured against the biofilms of E. coli (see Table 2). The oligomers (A)-(E) tested are oligo-(phenyl-ethynyl) compounds termed OPEs.

The MICs were measured for samples kept in the dark. The MBEC was measured in the dark (after 24 h incubation) and under light activation (1 h in an UV reactor). The MIC and MBEC values obtained were also compared to those of kanamycin, a well-known antibiotic commonly used against E. coli. The MBEC of kanamycin was only measured in the dark as it has no light induced activity. The MICs of the end-only OPEs (B)-(E) were lower than that of A with cationic side groups on the center aromatic. It was also observed that the oligomers (B) and (C) with DABCO side group showed significantly lower MIC compared to oligomers (D) and (E) with quaternary ammonium side groups. Note that oligomers (B) and (C) exhibit MIC values in the same range as kanamycin.

MBEC measurements showed similar trends with an increased concentration value that confirms the difficulties of completely eradicating the biofilm of E. coli compared to its inhibition. End-only oligomers (B)-(E) were again more efficient in killing biofilms compared to A. After 24 h incubation in the dark, (B) and (D) showed MBEC values around 150-200 µg/mL, five times lower than kanamycin. However (A) and (E) did not exhibit any dark killing of E. coli biofilm in the concentration range (<1000 µg/mL). All of the OPEs exhibited enhanced activity with 1 h near-UV light exposure, with MBEC values decreasing 3-4 times relative to the values for 24 h dark treatment. The MBEC value (light) of E is three fold greater than the other end-only OPEs (B)-(D). The later showed lower concentration (60-70 µg/mL) for the eradication of biofilms when incubated in the light for only an hour. However, despite these differences in MBEC, all end-only OPEs showed killing under light activation in concentration lower than 200 µg/mL. Also, all the biocidal activities of the end-only OPEs (B)-(E) with biofilms of E. coli were greater under light activation than in the dark. Note that OPE (A), which features side groups on the central arylene ring, did not show any killing in the concentration range for both the near-UV light exposure and the dark treatment.

When the activity is compared with the structures of the OPEs, it is clear that the DABCO side chains impart an increased activity against the biofilms compared to the quaternary ammonium side chains; the MIC and MBEC (light and dark) of (B) and (C) are always smaller or equal to those measured for (D) and (E). The MIC and MBEC of (A) is always the largest, which demonstrates that even with DABCO side groups its activity is lowered when the groups were attached to the center aromatic. When related to the formation of singlet oxygen, the correlation with the biocidal activity is more complex. Thus while (E) has the largest quantum yield for singlet oxygen generation, it has the smallest efficacy against biofilm of E. coli in the series of end-only OPEs. This result shows that not only the formation of singlet oxygen is necessary for light activated biocidal activity but also the oligomer structure and geometry play an important role. We have concluded in a previous study that the mechanism for light-activated bacterial killing includes both interaction with the membrane and outer envelope of the bacteria as well as the formation of singlet oxygen when the OPEs are in close proximity or attached to the bacteria.[16] The increase in the MBEC (light) for (E) despite its higher quantum yield could be attributed to its non-linear shape (thienylene ring on the center aromatic) combined with the lower activity ascribed to the quaternary ammonium side group (FIG. 4).

DOCUMENTS CITED (1) Lindsay, D.; von Holy, A. Bacterial biofilms within the clinical setting: what healthcare professionals should know, Journal of Hospital Infection 2006, 64, 313.

(2) Donlan, R. M. Biofilms: Microbial life on surfaces, Emerging Infectious Diseases 2002, 8, 881.

(3) Costerton, J. W.; Ellis, B.; Lam, K.; Johnson, F.; Khoury, A. E. Mechanism of Electrical Enhancement of Efficacy of Antibiotics in Killing Biofilm Bacteria, Antimicrobial Agents and Chemotherapy 1994, 38, 2803.

(4) Potera, C. Microbiology—Forging a link between biofilms and disease, Science 1999, 283, 1837.

(5) Antoci, V.; King, S. B.; Jose, B.; Parvizi, J.; Zeiger, A. R.; Wickstrom, E.; Freeman, T. A.; Cornposto, R. J.; Ducheyne, P.; Shapiro, I. M.; Hickok, N. J.; Adams, C. S. Vancomycin covalently bonded to titanium alloy prevents bacterial colonization, Journal of Orthopaedic Research 2007, 25, 858.

(6) Zhang, L. H.; Dong, Y. H. Quorum sensing and signal interference: diverse implications, Molecular Microbiology 2004, 53, 1563.

(7) Valle, J.; Da Re, S.; Henry, N.; Fontaine, T.; Balestrino, D.; Latour-Lambert, P.; Ghigo, J. M. Broad-spectrum biofilm inhibition by a secreted bacterial polysaccharide.

Proceedings of the National Academy of Sciences of the United States of America 2006, 103, 12558.
(8) Beckloff, N.; Laube, D.; Castro, T.; Furgang, D.; Park, S.; Perlin, D.; Clements, D.; Tang, H.; Scott, R. W.; Tew. G. N.; Diamond, G. Activity of an antimicrobial peptide mimetic against planktonic and biofilm cultures of oral pathogens, Antimicrobial Agents and Chemotherapy 2007, 51, 4125.
(9) Lu, T. K.; Collins, J. J. Dispersing biofilms with engineered enzymatic bacteriophage, Proceedings of the National Academy of Sciences of the United States of America 2007, 104, 11197.
(10) Eun, Y. J.; Weibel, D. B. Fabrication of Microbial Biofilm Arrays by Geometric Control of Cell Adhesion, Langmuir 2009, 25, 4643.
(11) Stewart, P. S.; Franklin, M. J. Physiological heterogeneity in biofilms, Nature Reviews Microbiology 2008, 6, 199.
(12) Pasquier, N.; Keul, H.; Heine, E.; Moeller, M. From multifunctionalized poly(ethylene imine)s toward antimicrobial coatings, Biomacromolecules 2007, 8, 2874.
(13) Zhou, Z. J.; Corbitt, T. S.; Parthasarathy, A.; Tang, Y. L.; Ista, L. F.; Schanze, K. S.; Whitten, D. G. "End-Only" Functionalized Oligo(phenylene ethynylene)s: Synthesis, Photophysical and Biocidal Activity, Journal of Physical Chemistry Letters 2010, 1, 3207.
(14) Wang, Y.; Corbitt, T. S.; Jett, S. D.; Tang, Y. L.; Schanze, K. S.; Chi, E. Y.; Whitten, D. G. Direct Visualization of Bactericidal Action of Cationic Conjugated Polyelectrolytes and Oligomers, Langmuir 2012, 28, 65.
(15) Gao, Y., and R. Cranston. 2008. Recent advances in antimicrobial treatment of textiles. Mat Research Journal 78:68-72.
(16) Zhou, Z. J.; Corbitt, T. S.; Parthasarathy, A.; Tang, Y. L.; Ista, L. F.; Schanze, K. S.; Whitten, D. G. "End-Only" Functionalized Oligo(phenylene ethynylene)s: Synthesis, Photophysical and Biocidal Activity, *Journal of Physical Chemistry Letters* 2010, 1, 3207.
(17) Ceri, H.; Olson, M. E.; Stremick, C.; Read, R. R.; Morck, D.; Buret, A. The Calgary Biofilm Device: New technology for rapid determination of antibiotic susceptibilities of bacterial biofilms, *Journal of Clinical Microbiology* 1999, 37, 1771.
(18) Olson, M. E.; Ceri. H.; Morck, D. W.; Buret, A. G.; Read, R. R. Biofilm bacteria: formation and comparative susceptibility to antibiotics, *Canadian Journal of Veterinary Research-Revue Canadienne De Recherche Veterinaire* 2002, 66, 86.
(19) Zhao, X. Y.; Pinto, M. R.; Hardison, L. M.; Mwaura, J.; Muller, J.; Jiang, H.; Witker, D.; Kleiman, V. D.; Reynolds, J. R.; Schanze, K. S. Variable band gap poly(arylene ethynylene) conjugated polyelectrolytes, *Macromolecules* 2006, 39, 6355.
(20) Harrison, J. J.; Stremick, C. A.; Turner, R. J.; Allan, N. D.: Olson, M. E.; Ceri, H. Microtiter susceptibility testing of microbes growing on peg lids: a miniaturized biofilm model for high-throughput screening, *Nature Protocols* 2010, 5, 1236.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of making an antimicrobial fiber for a woven or non-woven fabric, the fiber comprising a biocidal oligomer wherein the biocidal oligomer has the structure:

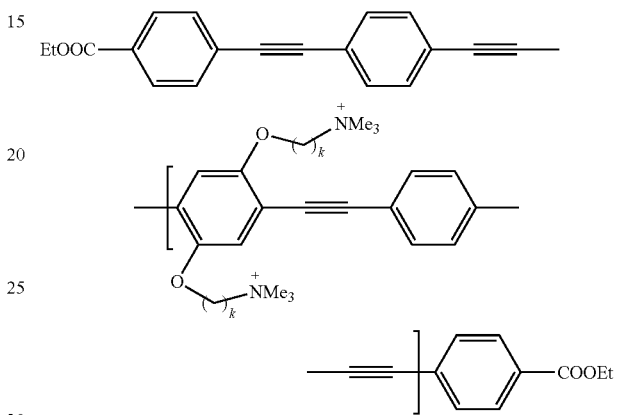

wherein $Z^-$ is an anion, k=1-6, and n=1-100;

the method comprising contacting a fiber-forming polymer and an effective amount of the biocidal oligomer; and, spinning a fiber from the fiber-forming polymer, to provide a fiber comprising the polymer and the biocidal oligomer.

2. The method of claim 1 wherein the spinning comprises a step of any one of meltblowing, melt spinning, dry spinning, wet spinning, gel spinning, single head electrospinning, multihead electrospinning, or flash spinning; the method optionally further comprising a step to orient the fibers, stretch the fibers, or both.

3. The method of claim 1, further comprising accumulating the fiber after spinning into a nonwoven mat.

4. The method of claim 1 wherein the polymer and the biocidal oligomer can react to form a covalently coupled biocidal oligomer-polymer composition.

5. The method of claim 1 wherein the polymer is polyester, a polyvinyl alcohol, a polyethylene oxide, a polyolefin, a cellulosic, a chitosan, an alginate, or a gelatin, or any mixture or blend thereof.

6. The method of claim 1 wherein the polymer comprises an azido group, and the biocidal oligomer and the polymer are mutually covalently reacted using click chemistry.

7. The method of claim 1 wherein e spun fiber comprising the biocidal oligomer possesses greater biocidal properties versus microorganisms in the presence of oxygen than does a comparable spun fiber lacking the biocidal oligomer.

8. The method of claim 1 wherein the biocidal properties of the spun fiber versus microorganisms in the presence of oxygen is increased under illumination by visible or ultraviolet light.

9. The method of claim 1, wherein the fiber-forming polymer and the biocidal oligomer are contacted prior to spinning a fiber from the fiber-forming polymer.

10. The method of claim 1, wherein the fiber-forming polymer and the biocidal oligomer are contacted subsequent to spinning a fiber from the fiber-forming polymer.

11. A fiber prepared by the method of claim 1.

12. A non-woven mat comprising the fiber of claim 11.

13. A surgical or wound dressing, a personal hygiene product, or a garment comprising the mat of claim 12.

14. A woven cloth comprising the fiber of claim 11.

15. A surgical or wound dressing, a personal hygiene product, or a garment comprising the woven cloth of claim 14.

* * * * *

UNITED STATES PATENT AND TRADEMARK OFFICE
CERTIFICATE OF CORRECTION

PATENT NO. : 9,549,549 B2
APPLICATION NO. : 14/233130
DATED : January 24, 2017
INVENTOR(S) : Whitten et al.

Page 1 of 1

It is certified that error appears in the above-identified patent and that said Letters Patent is hereby corrected as shown below:

In Column 46, Line 57, in Claim 7, delete "wherein e" and insert --wherein the--, therefor Signed and Sealed this
Tenth Day of April, 2018

Andrei Iancu
*Director of the United States Patent and Trademark Office*